United States Patent
Ghadiri et al.

(10) Patent No.: US 10,092,620 B2
(45) Date of Patent: Oct. 9, 2018

(54) USES OF CYCLIC PEPTIDES FOR TREATING AND PREVENTING ATHEROSCLEROSIS

(71) Applicant: THE SCRIPPS RESEARCH INSTITUTE, La Jolla, CA (US)

(72) Inventors: M. Reza Ghadiri, San Diego, CA (US); Luke J. Leman, Encinitas, CA (US); Yannan Zhao, La Jolla, CA (US); Bruce E. Maryanoff, Holicong, PA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/781,859

(22) PCT Filed: Apr. 2, 2014

(86) PCT No.: PCT/US2014/032620
§ 371 (c)(1),
(2) Date: Oct. 1, 2015

(87) PCT Pub. No.: WO2014/165563
PCT Pub. Date: Oct. 9, 2014

(65) Prior Publication Data
US 2016/0250280 A1   Sep. 1, 2016

Related U.S. Application Data

(60) Provisional application No. 61/807,589, filed on Apr. 2, 2013.

(51) Int. Cl.
*A61K 38/00* (2006.01)
*A61K 38/12* (2006.01)

(52) U.S. Cl.
CPC .................................... *A61K 38/12* (2013.01)

(58) Field of Classification Search
None
See application file for complete search history.

(56) References Cited

U.S. PATENT DOCUMENTS

2013/0005644 A1 *   1/2013   Fairlie ................. C07K 14/472
514/1.4

* cited by examiner

*Primary Examiner* — Jeannette M Lieb
(74) *Attorney, Agent, or Firm* — Hugh Wang; Thomas Fitting

(57) ABSTRACT

The present invention provides cyclic compounds that are useful in preventing or treating atherosclerosis or related disorders. The invention also provides therapeutic methods for treating or preventing various diseases or disorders associated with or mediated by atherosclerosis. Further provided in the invention are methods of screening for anti-atherosclerotic cyclic peptides with improved properties.

7 Claims, 9 Drawing Sheets
Specification includes a Sequence Listing.

USES OF CYCLIC PEPTIDES FOR TREATING AND PREVENTING ATHEROSCLEROSIS

CROSS-REFERENCE TO RELATED APPLICATIONS

The subject patent application claims the benefit of priority to U.S. Provisional Patent Application No. 61/807,589, filed Apr. 2, 2013. The full disclosure of the priority application is incorporated herein by reference in its entirety and for all purposes.

STATEMENT OF GOVERNMENT SUPPORT

This invention was made with government support under Grant No. HL104462 awarded by the National Institutes of Health. The U.S. Government therefore has certain rights in the invention.

BACKGROUND OF THE INVENTION

Cardiovascular problems represent the major cause of death and disability in the developed world. Atherosclerosis is associated with the development of many cardiovascular disorders. Atherosclerosis is characterized by the deposits or plaques of lipids and other blood derivatives in the arterial walls of, e.g., aorta, coronary arteries and carotid. Atherosclerotic plaques begin as fatty streaks underlying the endothelium of large arteries. Recruitment of macrophages and their subsequent uptake of LDL derived cholesterol are the major cellular events contributing to fatty streak formation. These plaques can be calcified to a greater or lesser extent according to the progression of the process. They are also associated with the accumulation of fatty deposits consisting mainly of cholesterol esters in the arteries. Cholesterol accumulates in the foam cells of the arterial wall, thereby narrowing the lumen and decreasing the flow of blood. This is accompanied by a thickening of the arterial wall, with hypertrophy of the smooth muscle, the appearance of foam cells and the accumulation of the fibrous tissue. Hypercholesterolemia can therefore result in very serious cardiovascular pathologies such as infarction, peripheral vascular disease, stroke, sudden death, cardiac decompensation, cerebral vascular accidents and the like.

There is a recognized need in the art for better and more reliable means for treating and preventing atherosclerosis and medical conditions that are associated with or mediated by atherosclerosis. The present invention is directed to this and other needs.

SUMMARY OF THE INVENTION

In one aspect, the invention provides methods for treating or preventing atherosclerosis or a disorder associated with or mediated by atherosclerosis in a subject afflicted with or at risk of developing atherosclerosis or a related disorder. In a related aspect, the invention provides methods for reducing total cholesterol level, reducing LDL level and/or VLDL level, or enhancing HDL level in a subject. All these methods entail administering to the subject a pharmaceutical composition that contains a therapeutically effective amount of a cyclic peptide having a sequence of from four to about sixteen amino acid residues or analogs thereof, which are alternating D- and L-residues along partial or entire sequence of the peptide. Diseases or disorders suitable for treatment with the methods include, e.g., hypercholesterolemia, cardiovascular disorders, atherosclerotic vascular diseases, cerebrovascular diseases, aneurysm, peripheral vascular diseases and intermittent claudication. Depending on the specific disease to be treated, the pharmaceutical composition can be administered to the subject via various means, e.g., orally, intravenously, subcutaneously or intraperitoneally.

In some embodiments of the invention, the cyclic peptide contains alternating D- and L-α-amino acid residues along its entire sequence. In some embodiments, the cyclic peptide compound employed in the pharmaceutical composition has a sequence formula of c[B-J-U1-X-U2-Z]. In this sequence, "B" is a peptide segment comprising at least 2 hydrophobic amino acid residues or analogs thereof; and "J" is or contains a positively charged amino acid residue, a polar uncharged amino acid residue, or an analog thereof. Additionally, one or both of "U1" and "U2" in the sequence formula is or harbors a negatively charged amino acid residue, a polar uncharged amino acid residue or analog thereof. Flanked by U1 and U2, "X" is or contains a polar uncharged amino acid residue, a His residue or an analog thereof. Finally, "Z" is or contains Asn, Gln, a charged amino acid residue, or an analog thereof. Examples of such cyclic peptide include c[wLwReQeR] (SEQ ID NO:1), c[wLwSeQsO] (SEQ ID NO:4), or c[wLwSeQhK] (SEQ ID NO:40).

In some of these embodiments, the hydrophobic segment "B" can consist of 2, 3, 4, 5, 6, or 7 hydrophobic amino acid residues or analogs thereof. In some preferred embodiments, "B" consists of 3 hydrophobic amino acid residues or analogs thereof. For example, "B" can be $^D$Trp-Leu-$^D$Trp, $^D$Tyr-Leu-$^D$Tyr, $^D$Trp-Trp-$^D$Trp, $^D$Phe-Leu-$^D$Trp, Trp-$^D$Leu-Trp, Tyr-$^D$Leu-Tyr, Trp-$^D$Trp-Trp, or Phe-$^D$Leu-Trp. In some embodiments, "J" represents Lys, Arg, Ser, His, Orn (ornithine), diaminobutyric acid or diaminopropionic acid. In some other embodiments, "J" is naphthylalanine (Nal), homoleucine (Hml), or 2-amino-octanoic acid (Aoc). In some cyclic peptides employed for the invention, the U1 and U2 moieties in the above noted sequence formula are each independently a $^D$Asp, $^D$Glu or $^D$Ser residue. In some embodiments, the "X" moiety corresponds to an Asn or Gln residue. In some embodiments, the "Z" moiety represents a positively charged residue, e.g., Lys, Arg, His, Orn (ornithine) or diaminobutyric acid.

In some methods of the invention, the employed cyclic peptide compound has a sequence formula of c[B-J-U1-X-U2-Z], wherein B consists of $^D$Trp-Leu-$^D$Trp or $^D$Tyr-Leu-$^D$Tyr; J is Lys, Arg, or Ser; U1 and U2 are each independently a $^D$Asp, $^D$Glu or $^D$Ser residue; X is Asn or Gln; and Z is Lys, Arg, Orn (ornithine) or diaminobutyric acid.

Some specific examples of cyclic peptides that can be employed in the invention include c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[fWwYqHhQ] (SEQ ID NO:5), c[LwLwLrKe] (SEQ ID NO:6), c[wLwZeQeK] (SEQ ID NO:7), c[wLwKdNdK] (SEQ ID NO:8), c[wLwRdNdK] (SEQ ID NO:9), c[wLwKdQdK] (SEQ ID NO:10), c[wLwKeNeK] (SEQ ID NO:11), c[wLwHeNeK] (SEQ ID NO:12), c[wLwOeQeO] (SEQ ID NO:13), c[wL$^{Me}$wSeQ$^{Me}$sO] (SEQ ID NO:14), c[wLwOeNeO] (SEQ ID NO:19), and c[wLwSeQhK] (SEQ ID NO:40). Some other examples of peptides suitable for the invention include c[fWwYqHhQ] (SEQ ID NO:5), c[(Me)wLwR(Me)eQeR] (SEQ ID NO:46), c[WIWwkhkh] (SEQ ID NO:47), c[wFyYhOrS] (SEQ ID NO:48), c[(PA)wLlHsKk] (SEQ ID NO:49), c[WIWrEqEr] (SEQ ID NO:50), c[fWwYtRhS (SEQ ID NO:51)], c[wFfYrHhS] (SEQ ID NO:52), and c[wLwKhShK] (SEQ ID NO:53).

Some methods of the invention employ a cyclic peptide that has a sequence formula of c[wLw-J-u1-X-u2-Z] and contains about 8 alternating D- and L-form of amino acid residues or amino acid analogs. In this sequence formula, "wLw" denotes a tripeptide segment consisting of $^D$Trp-Leu-$^D$Trp; J is serine or a positively charged amino acid residue or analog; u1 and u2 are each independently a $^D$Asp, $^D$Glu or $^D$Ser residue; X is Asn residue or Gln residue; and Z is a positively charged amino acid residue or analog. In some embodiments, J is Lys, Arg, His, Ser, Orn (ornithine), diaminobutyric acid or diaminopropionic acid. In some embodiments, Z is Lys, Arg, or Orn (ornithine).

In a related aspect, the invention provides pharmaceutical combinations or kits for treating or preventing in a subject atherosclerosis or a disorder associated with or mediated by atherosclerosis. The pharmaceutical combinations or kits contain at least a cyclic peptide that has a sequence of from four to about sixteen D- and L-α-amino acids and possess anti-atherosclerotic activity. The amino acid residues or analogs thereof are alternating D- and L-residues along partial or entire sequence of the peptide. In some embodiments, the cyclic peptide compound has a sequence formula of c[B-J-U1-X-U2-Z], wherein B is a peptide segment comprising at least 2 hydrophobic amino acid residues or analogs thereof; J comprises a positively charged amino acid residue, a polar uncharged amino acid residue, or an analog thereof; one or both of U1 and U2 comprise a negatively charged amino acid residue, a polar uncharged amino acid residue or analog thereof; X comprises a polar uncharged amino acid residue, a His residue or an analog thereof; and Z comprises Asn, Gln, a charged amino acid residue, or an analog thereof; and wherein amino acid residues or analogs of the cyclic peptide are alternating D- and L-residues along the entire sequence of the cyclic peptide.

In another aspect, the invention provides uses of a cyclic peptide having a sequence of from four to about sixteen D- and L-α-amino acids in an amount effective for treating or preventing atherosclerosis or a disorder associated with or mediated by atherosclerosis in a subject. The amino acid residues or analogs thereof in the peptide are alternating D- and L-residues along partial or entire sequence of the peptide. In some embodiments, the employed cyclic peptide compound has a sequence formula of c[B-J-U1-X-U2-Z], wherein B is a peptide segment comprising at least 2 hydrophobic amino acid residues or analogs thereof; J comprises a positively charged amino acid residue, a polar uncharged amino acid residue, or an analog thereof; one or both of U1 and U2 comprise a negatively charged amino acid residue, a polar uncharged amino acid residue or analog thereof; X comprises a polar uncharged amino acid residue, a His residue or an analog thereof; and Z comprises Asn, Gln, a charged amino acid residue, or an analog thereof; and wherein amino acid residues or analogs of the cyclic peptide are alternating D- and L-residues along the entire sequence of the cyclic peptide.

In a further aspect, the invention provides novel cyclic peptides with anti-atherosclerotic activities. The peptide each contains from about four to about sixteen amino acid residues or analogs, which are alternating D- and L-α-residues along partial or entire sequence of the peptide. Some of the peptides fall under a sequence formula of c[B-J-U1-X-U2-Z]. In this sequence formula, B is a peptide segment comprising at least 2 hydrophobic amino acid residues or analogs thereof; J comprises a positively charged amino acid residue, a polar uncharged amino acid residue, or an analog thereof; one or both of U1 and U2 comprise a negatively charged amino acid residue, a polar uncharged amino acid residue, a His residue or an analog thereof; and Z comprises Asn, Gln, a charged amino acid residue, or an analog thereof. Typically, alternating D- and L-residues or analogs are present along the entire sequence of the cyclic peptides. Examples of the cyclic peptides of the invention are shown in FIG. 1 and Table 1.

A further understanding of the nature and advantages of the present invention may be realized by reference to the remaining portions of the specification and claims.

DETAILED DESCRIPTION OF THE INVENTION

I. Overview

Figure 1:
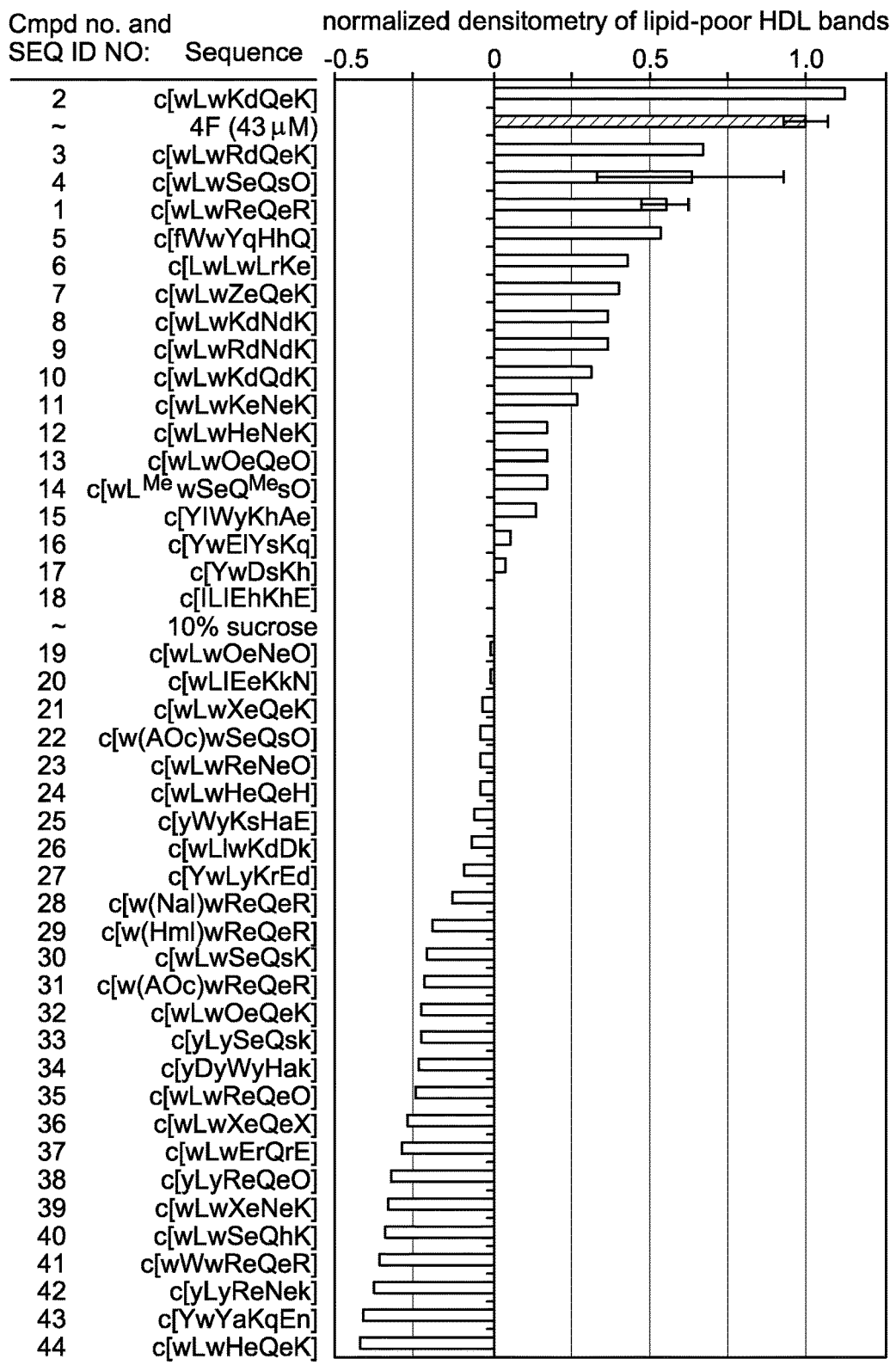
FIG. 1 shows relative activities of cyclic D,L-α-peptides ranked according to their effectiveness in increasing the level of lipid-poor HDLs in human plasma in vitro. Lipid-poor HDL particles are key initial acceptors of cholesterol in reverse cholesterol transport. Peptides were screened at 360 µM from 10% sucrose/H$_2$O stocks. Peptide 4F was used as a positive control. The data from individual blots were normalized for ranking by using the 10% sucrose and 4F samples. Error bars representing SD are shown for peptides that were included on each of the four gels required to complete analysis of the full panel. Capital letters represent L-amino acids; small letters represent D-amino acids. Superscript Me denotes an N-methylated amino acid. Abbreviations: Aoc, 2-amino-octanoic acid; Hml, homoleucine; Nal, naphthylalanine; O, ornithine; X, diaminobutyric acid; Z, diaminopropionic acid. SEQ ID NOs of the peptides, which are respectively identical to the compound numbers of the peptides, are noted in the figure.

The present invention is predicated in part on the development by the present inventors of self-assembling cyclic D,L-α-peptides which were shown to have anti-atherosclerotic activities. These cyclic peptides demonstrated activities in reducing plasma cholesterol level, promoting HDL mediated reverse cholesterol transport, and preventing the development of atherosclerotic lesions. Specifically, as detailed herein, the inventors explored a supramolecular approach to identify potential agents to treat atherosclerosis involving cyclic D,L-α-peptides that can self-assemble into nanotube architectures and mimic the lipid binding and functional properties of apolipoprotein A-I (apoA-I). Certain 8-residue cyclic D,L-α-peptides promoted cholesterol efflux from macrophage cells and remodeled mature high-density lipoprotein (HDL) particles into nascent lipid-poor HDLs in vitro and in vivo. Oral administration of the cyclic peptides (e.g., c[wLwReQeR] (SEQ ID NO:1)) in drinking water ad libitum to low-density lipoprotein receptor (LDLr)-null mice fed a high-fat diet for 10 weeks reduced total plasma cholesterol levels by up to 55% and inhibited the development of atherosclerotic lesions in the aortic sinus by 50% (vs. controls). In vitro and in vivo anti-atherosclerotic activities of some other cyclic peptides were also demonstrated by the inventors.

Not to be bound in theory, the observed anti-atherogenicity could involve the promotion of reverse cholesterol transport by the cyclic D,L-α-peptides. Alternatively, the cyclic D,L-α-peptides could act on a target (or targets) in the intestine. Regardless of the underlying mechanism, the inventors' studies demonstrate that it would be possible to modulate HDL morphology and function by using appropriately designed, membrane-active nanotubes self-assembled from cyclic D,L-α-peptides. The studies further suggest that the cyclic D,L-α-peptides can promote remodeling of HDL to lipid-poor particles and cellular cholesterol efflux, two important aspects of the reverse cholesterol transport pathway, thereby lowering total plasma cholesterol and preventing atherosclerotic lesion development.

The membrane-active cyclic D,L-α-peptides of the invention can be derived from a very large sequence space of natural and unnatural amino acids. There is great potential for further structure-activity optimization to identify analog peptides with improved activity. The cyclic D,L-α-peptides of the invention are generally proteolytically stable and easy to synthesize. These low-molecular-weight cyclic peptides provide an attractive new approach in developing potential therapeutic agents for atherosclerosis.

In accordance with these discoveries, the present invention provides novel cyclic peptides which are capable of treating/preventing atherosclerosis or inhibiting progression of atherosclerotic lesions. As detailed herein, some of the self-assembling D,L-α-peptides of the invention contain alternating L- and D-residues in their sequences. The membrane-active cyclic D,L-α-peptides can be derived from a very large sequence space of natural and unnatural amino acids. In addition, the cyclic D,L-α-peptides of the invention are generally proteolytically stable and easy to synthesize. These low-molecular-weight cyclic peptides represent attractive new therapeutic agents for atherosclerosis. Also provided in the invention are therapeutic uses or methods for employing these peptides in preventing or treating diseases or disorders that are mediated by or associated with atherosclerosis. Examples of such diseases include myocardial infarction and stroke. Typically, these therapeutic methods entail administering to a subject afflicted with such a disease a pharmaceutical composition that contains a therapeutically effective amount of an anti-atherosclerosis cyclic peptide disclosed herein. Further provided in the invention are methods to identify additional anti-atherogenicity agents with improved activities.

More detailed guidance for practicing the invention is provided in the following sections.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press (4th ed., 2000). In addition, the following definitions are provided to assist the reader in the practice of the invention.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

Amino acids having both the amine and carboxylic acid groups attached to the first ($\alpha$-) carbon atom have particular importance in biochemistry. They include the 23 "proteinogenic" ("protein-building") amino acids which combine into peptide chains to form the building blocks of a vast array of proteins. These are all L-stereoisomers ("left-handed" isomers) although a few D-amino acids ("right-handed") occur in bacterial envelopes and some antibiotics. 20 of the 23 proteinogenic amino acids are encoded directly by triplet codons in the genetic code and are known as "standard" amino acids. The other three ("non-standard" or "non-canonical") are pyrrolysine (found in methanogenic organisms and other eukaryotes), selenocysteine (present in many noneukaryotes as well as most eukaryotes), and N-Formylmethionine.

Of the standard $\alpha$-amino acids, all but glycine can exist in either of two enantiomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum, as in exotic sea-dwelling organisms such as cone snails. They are also abundant components of the peptidoglycan cell walls of bacteria, and D-serine may act as a neurotransmitter in the brain.

Aside from the 23 proteinogenic amino acids, there are many other amino acids that are called non-proteinogenic or non-standard. Those either are not found in proteins (for example carnitine and gamma-aminobutyric acid), or are not produced directly and in isolation by standard cellular machinery (for example, hydroxyproline and selenomethionine). Non-standard amino acids that are found in proteins are formed by posttranslational modification, which is modification after translation during protein synthesis. Some nonstandard amino acids are not found in proteins. Examples include lanthionine, 2-aminoisobutyric acid, dehydroalanine, and the neurotransmitter gamma-aminobutyric acid (GABA). Non-standard amino acids often occur as intermediates in the metabolic pathways for standard amino acids—for example, ornithine and citrulline occur in the urea cycle, part of amino acid catabolism.

The side-chain of an amino acid can make it a weak acid or a weak base, and a hydrophile if the side-chain is polar or a hydrophobe if it is nonpolar. Amino acids can be classified by the properties of their side-chain into non-polar hydrophobic residues, polar but uncharged hydrophilic residues, and polar charged residues. Among the 20 standard proteinogenic amino acids, non-polar hydrophobic residues include alanine, glycine, valine, leucine, isoleucine, proline, phenylalanine, and methionine. Polar uncharged residues include asparagine, glutamine, serine, threonine, tyrosine, cysteine and tryptophan. Polar and charged amino acids include positively charged basic residues (lysine, arginine and histidine) and negatively charged acidic residues (aspartic acid and glutamic acid).

As used herein, "amino acid residues or analogs thereof" encompass naturally occurring amino acids, including both proteinogenic and non-proteinogenic amino acids. Naturally occurring amino acids are those encoded by the genetic code, as well as those amino acids that are later posttranslationally modified (e.g., hydroxyproline, $\gamma$-carboxyglutamate, and O-phosphoserine) or otherwise naturally existing in nature. In addition to natural amino acid residues, amino acid residues or analogs present in the cyclic peptides of the invention also encompass non-naturally existing amino acid analogs or derivatives, e.g., synthetic amino acid derivatives and amino acid mimetics that function in a manner similar to the naturally occurring amino acids. The term "amino acid residues or analogs" specifically encompasses both L-form and D-form of amino acid residues. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Typically, the cyclic peptides of the invention harbor both L-form and D-form of proteinogenic or non-proteinogenic residues, as well as other amino acid derivative or analogs.

The term "analog" or "derivative" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs to identify variants of known compounds having improved traits (such as higher binding affinity for a target molecule) is an approach that is well known in pharmaceutical chemistry.

Administration "in conjunction with" one or more other therapeutic agents includes simultaneous (concurrent) and consecutive administration in any order.

"Atherosclerosis" refers to a condition characterized by the hardening and/or narrowing of the arteries caused by the buildup of atheromatous plaque inside the arterial walls. The atheromatous plaque is divided in three components, (1) the atheroma, a nodular accumulation of a soft flaky material at the center of large plaques, composed of macrophages nearest the lumen of the artery; (2) underlying areas of cholesterol crystals; (3) calcification at the outer base of more advanced lesions. Indicators of atherosclerosis include, for example, the development of plaques in the arteries, their calcification, the extent of which can be determined by Sudan IV staining, or the development of foam cells in arteries. The narrowing of the arteries can be determined by coronary angioplasty, ultrafast CT, or ultrasound.

The term "contacting" has its normal meaning and refers to combining two or more agents (e.g., polypeptides or small molecule compounds) or combining agents and cells. Contacting can occur in vitro, e.g., combining two or more agents or combining an agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate. Contacting can also occur inside the body of a subject, e.g., by administering to the subject an agent which then interacts with the intended target (e.g., a tissue or a cell).

"Myocardial injury" means injury to the muscular tissue of the heart. It may be either an acute or nonacute injury in terms of clinical pathology. In any case it involves damage to cardiac tissue and typically results in a structural or compensatory response. Unless otherwise noted, myocardial injury as used herein primarily refers to acute myocardial injury such as acute myocardial infarction (heart attack) and cardiac ischemia/reperfusion.

Acute myocardial infarction (AMI or MI), commonly known as a heart attack, is a disease state that occurs when the blood supply to a part of the heart is interrupted. The resulting ischemia or oxygen shortage causes damage and potential death of heart tissue.

Ischemia is a restriction in blood supply, generally due to factors in the blood vessels, with resultant damage or dysfunction of tissue (e.g., tissues of the heart, lung, and liver). Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

Stroke is the clinical designation for a rapidly developing loss of brain function due to an interruption in the blood supply to all or part of the brain. Interruption in the blood supply results in depletion of oxygen and glucose in the affected area. This immediately reduces or abolishes neuronal function, and also initiates an ischemic cascade which causes neurons to die or be seriously damaged, further impairing brain function. Stroke can be caused by, e.g., thrombosis, embolism, or hemorrhage.

The term "subject" for purposes of treatment refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., atherosclerosis, or a disorder associated with or mediated by atherosclerosis such as stroke or myocardial dysfunction), alleviating the symptoms or arresting or inhibiting further development of the disease, condition, or disorder. Subjects in need of treatment include those already suffering from the disease or disorder. They also encompass ones who are at risk of developing the disorder, e.g., one at risk of developing atherosclerosis following intervention for an occlusive event. Treatment may be prophylactic (to prevent or delay the onset of the disease, or to prevent the manifestation of clinical or subclinical symptoms thereof) or therapeutic suppression or alleviation of symptoms after the manifestation of the disease. In the treatment of a disease or disorder associated with or mediated by atherosclerosis, a therapeutic agent may directly decrease the pathology of the disease, or render the disease more susceptible to treatment by other therapeutic agents.

A "therapeutically effective amount" is intended for a minimal amount of active agent which is necessary to impart therapeutic benefit to a subject. Thus, a "therapeutically effective amount" administered to a subject is such an amount which induces, ameliorates or otherwise causes an improvement in the pathological symptoms, disease progression or physiological conditions associated with a disorder or resistance to succumbing to a disorder.

Disorders or diseases mediated by or associated with atherosclerosis refer to any clinical condition that has atherosclerosis as an important underlying factor or manifesting symptom at any stage of its development (e.g., onset and progression). These can broadly encompass hypercholesterolemia (e.g., coronary heart diseases), atherosclerotic vascular diseases (AVD) such as ischemic heart diseases (e.g., angina and myocardial infarction), cerebrovascular diseases (e.g., stroke and transient ischemic attacks), aneurysms, high blood pressure, thrombosis, and other peripheral vascular diseases and intermittent claudication.

III. Cyclic Peptides for Treating Atherosclerosis

High-density lipoproteins (HDL) nanoparticles are complexes of lipids and proteins that eliminate cholesterol from the bloodstream, thereby reducing atherosclerotic plaque burden. HDL particles are formed in vivo when apoA-I, a 243-amino-acid protein consisting of ten amphiphilic α-helices, interacts with phospholipids, cholesterol, and other proteins. Anti-atherogenicity of apoA-I was demonstrated by observations that i.v. infusions of apoA-I or reconstituted HDL particles, or over-expression of apoA-I, exhibit protective effects. However, the use of apoA-I itself as a therapeutic agent has not been feasible. This is because the large amounts of protein (>3 g/single infusion) required are cost prohibitive, given current production methods. In addition, apoA-I is not orally bioavailable, so an i.v. route of administration limits its general use.

The invention provides therapeutic methods of using cyclic peptides to treat or prevent atherosclerosis and related diseases or disorders. Preferably, cyclic peptides employed in the methods of the invention can mimick apoA-I in its activities of forming HDL nanoparticles. Underscoring the structure of some cyclic peptides suitable for the invention is that some of the structural roles of apoA-I might not be easily mimicked by single or dimeric helical peptides. For example, apoA-I adapts to various particle sizes and morphologies during the course of HDL maturation from small, discoidal particles deficient in cholesterol and triglycerides to larger, cholesterol/triglyceride-rich spherical particles. ApoA-I is also central to HDL metabolism, which entails apolipoprotein dissociation, HDL particle fusion, and HDL interactions with enzymes and membrane transporters. Instead, it was conceived that the structural and functional properties of apoA-I might be effectively mimicked by supramolecular peptide structures. Such structures would possess inherent structural adaptability by virtue of environmentally dependent, dynamic self-assembly.

As exemplified by peptide c[wLwReQeR] (SEQ ID NO:1) (Compound 1 or peptide 1 as denoted herein), the cyclic peptides of the invention can adopt flat, ring-shaped conformations in which the backbone amide groups are oriented perpendicular to the side chains and the plane of the ring. Under conditions that favor hydrogen bonding, such as adsorption onto lipid membranes, cyclic D,L-α-peptides can stack to form hollow, β-sheet-like tubular structures with the amino acid side chains on the outside surface of the nanotube. Importantly, the self-assembly is reversible, such that a highly dynamic assembly process takes place. The side chains on the self-assembled nanotube surface have certain similarities to the side chain display in an α-helix. The distance between neighboring side chains in a peptide nanotube (α-carbon distance of 4.7-5.1 Å) is similar to that between the i and i+3 residues in an α-helix (α-carbon distance of 5.0-5.3 Å). Also relevant to the design of the peptides is that structural models of apoA-I within discoidal and spherical HDLs involve two side-by-side helical segments wrapped around a phospholipid bilayer in a double-belt motif. Nanotubes constructed from 8-residue cyclic D,L-α-peptide will likely have the appropriate dimensions and side chain topology to effectively mimic the helical dimer topology of apoA-I in the HDL setting.

According to the invention, membrane-active nanotubes can be created from cyclic D,L-α-peptides that could modulate HDL morphology and function through dynamic HDL nanoparticle remodeling. As detailed herein, compounds generated with such a supramolecular approach not only promote cholesterol efflux from macrophages and remodel mature HDL into nascent lipid-poor HDL, but also markedly reduced atherosclerotic lesions in high-fat-fed, low-density lipoprotein receptor (LDLr)-null mice in a 10-week, oral-dosing study.

There are many cyclic peptides that can be readily employed or modified in the practice of the methods of the invention. Typically, the cyclic peptides employed in the invention are self-assembling D,L-α-peptides and comprise a sequence of from four to about sixteen amino acid residues or analogs thereof (including pharmaceutically acceptable salt derivatives). Typically, the amino acid residues or analogs thereof present in the cyclic peptides are alternating D- and L-residues along partial or entire sequence of the peptide. In some embodiments, the cyclic peptides have from about six to about ten or twelve alternating D- and L-α-amino acids. In other embodiments, the cyclic peptides having about six or eight alternating D- and L-α-amino acids are employed. Preferably, amino acid residues of the cyclic peptide are alternating D- and L-residues as present in the entire sequence of the peptide. Examples of such peptides are described herein in the Examples below. Additional cyclic peptides that may be used in the invention are described, e.g., in PCT publications WO 95/10535, WO 03/092631, and WO 03/092632. Preferably, the cyclic peptides employed in the invention have minimum or no undesired toxicity against normal mammalian cells, which can be determined, e.g., by hemolysis of erythrocytes.

In some preferred embodiments, cyclic peptides employed in the methods of the invention fall under a sequence formula of c[B-J-U1-X-U2-Z]. In this sequence formula, B is a hydrophobic peptide segment containing at least 2 hydrophobic amino acid residues or analogs thereof. J is moiety containing a positively charged amino acid residue, a polar uncharged amino acid residue, or an analog thereof. In addition, one or both of U1 and U2 contains a negatively charged amino acid residue, a polar uncharged amino acid residue or analog thereof. Flanked by U1 and U2, X moiety or segment represents the center of a polar face or segment of the cyclic peptide and typically contains a polar uncharged amino acid residue, a His residue or an analog thereof. Finally, at the end of the sequence formula of the cyclic peptide, Z moiety or segment contains Asn, Gln, a charged amino acid residue, or an analog thereof.

In some embodiments, the hydrophobic peptide segment B consists of 2, 3, 4, 5, 6 or 7 hydrophobic amino acid residues or analogs thereof. In some preferred embodiments, hydrophobic peptide segment consists of 3 hydrophobic amino acid residues or analogs thereof. Specific examples of the cyclic peptides of the invention are shown in FIG. 1, e.g., c[wLwReQeR] (SEQ ID NO:1), c[wLwSeQsO] (SEQ ID NO:4) and c[wLwSeQhK] (SEQ ID NO:40). In addition to these specific peptides shown in FIG. 1, derivative peptides which have conservative amino acid substitutions relative to the sequence of the exemplified peptides are also encompassed by the invention.

Some cyclic peptides suitable for use in the therapeutic applications of the invention contain a hydrophobic peptide segment $^D$Trp-Leu-$^D$Trp, $^D$Tyr-Leu-$^D$Tyr, $^D$Trp-$^D$Trp-$^D$Trp, or $^D$Phe-Leu-$^D$Trp. In some other peptides, the hydrophobic segment contains an enantiomeric tripeptide, e.g., Trp-$^D$Leu-Trp, Tyr-$^D$Leu-Tyr, Trp-$^D$Trp-Trp, or Phe-$^D$Leu-Trp. In some cyclic peptides of the invention, the peptide moiety or segment J, which is adjacent to the hydrophobic segment B, is a single serine residue or a single positively charged residue such as Lys, Arg, His, Orn (ornithine), diaminobutyric acid or diaminopropionic acid. In some other embodiments, J is an amino acid analog or derivative such as naphthylalanine (Nal), homoleucine (Hml), or 2-aminooctanoic acid (Aoc). In some preferred cyclic peptides of the invention, U1 and U2 are each independently a $^D$Asp, $^D$Glu or $^D$Ser residue. In some embodiments, these two acidic or neutral Ser residues are separated by an Asn or Gln residue (X) located in the center of a polar segment of the cyclic peptide. In some preferred embodiments, a positively charged natural or unnatural residue (Z) is present at the end of the sequence of the cyclic peptides, e.g., Lys, Arg, His, Orn (ornithine) or diaminobutyric acid.

Some preferred cyclic peptide compounds of the invention are comprised of about 8 alternating D- and L-form of amino acid residues or (unnatural) amino acid analogs. These peptides have a sequence that falls under the formula c[wLw-J-u1-X-u2-Z]. In this sequence formula, "wLw" denotes a tripeptide segment consisting of $^D$Trp-Leu-$^D$Trp; J is a positively charged amino acid residue or amino acid analog, or serine residue; u1 and u2 are each independently a $^D$Asp, $^D$Glu or $^D$serine residue; X is Asn residue or Gln residue; and Z is Lys, Arg, His, Orn (ornithine) or diaminobutyric acid. Specific examples of such cyclic peptides include c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[wLwZeQeK] (SEQ ID NO:7), c[wLwKdNdK] (SEQ ID NO:8), c[wLwRdNdK] (SEQ ID NO:9), c[wLwKdQdK] (SEQ ID NO:10), c[wLwKeNeK] (SEQ ID NO:11), c[wLwHeNeK] (SEQ ID NO:12), c[wLwOeQeO] (SEQ ID NO:13), and c[wLwOeNeO] (SEQ ID NO:19).

In some other embodiments, the cyclic peptides do not contain the alternating positively charged and negatively charged residues as described above. Rather, they can be comprised entirely of, e.g., positively charged and/or uncharged residues. An example of such peptides is c[wLwKhShK] (SEQ ID NO:53). As shown in the Examples herein, such peptides can also exhibit anti-atherosclerotic activities required for the therapeutic methods of the present invention.

In some other embodiments, residues of the cyclic peptides with anti-atheroscletotic activities of the invention are not alternating D- and L-α-residues throughout the entire sequence of the peptides. Instead, they may have contiguous D- or L-α-amino acid residues in parts of their sequences. For example, peptides c[WlWwkhkh] (SEQ ID NO:47) and c[WIWrEqEr] (SEQ ID NO:50) were shown to have excellent activities in generating plasma pre-beta HDL. Additional examples of such peptides are shown in Table 1.

Figure 8:
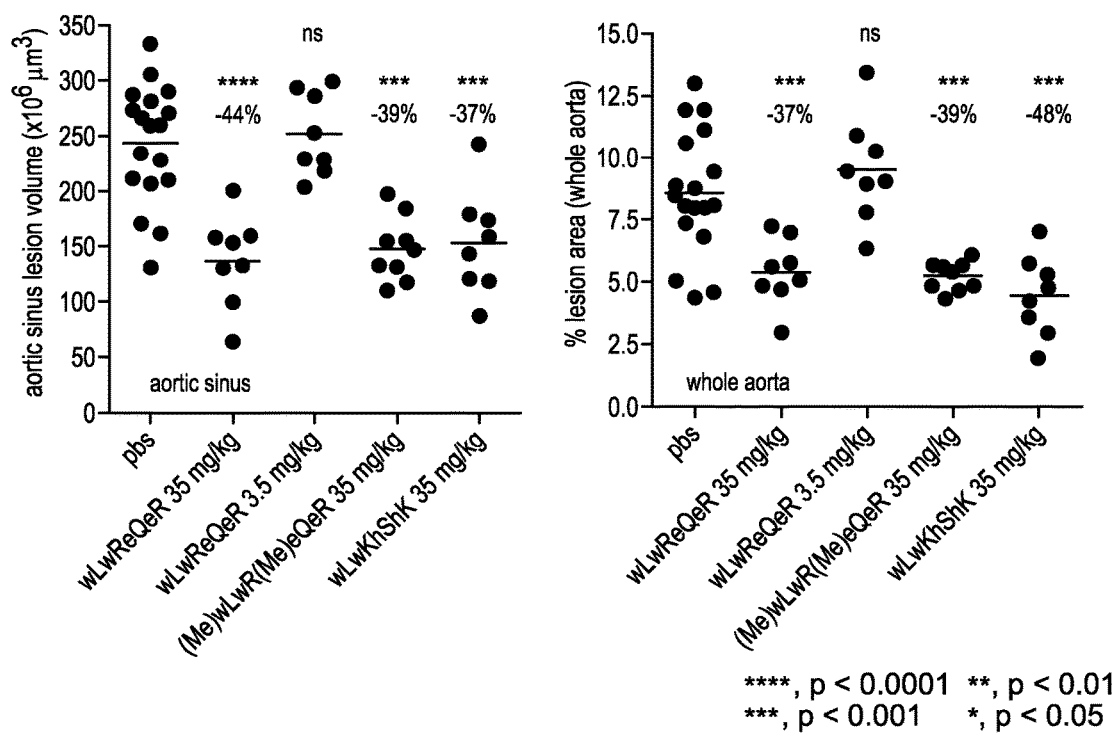
FIG. 8 shows that oral administration of several peptides can reduce the development of atherosclerotic legions in mice. The cyclic peptides used in the study are wLwReQeR (SEQ ID NO:1), wLwSeQhK (SEQ ID NO:40), (Me)wLwR(Me)eQeR (SEQ ID NO:46), and wLwKhShK (SEQ ID NO:53).

In some embodiments, a derivative or analog of the specific cyclic peptides exemplified herein (e.g., peptides shown in FIG. 1 and Table 1) can be used. For example, the peptides can be alkylated at one or more of its residues. As an example, a derivative of peptide c[wLwReQeR] (SEQ ID NO:1), in which two backbone amide moieties are methylated, (Me)wLwR(Me)eQeR (SEQ ID NO:46), is suitable for the invention. As demonstrated herein, such derivative peptides can be similarly effective as the parent compound in preventing the development of atherosclerotic lesions (FIG. 8).

In some embodiments, the cyclic peptides contains a hydrophobic peptide segment consisting of 4 hydrophobic residues. Examples of such peptides include fWwYtRhS (SEQ ID NO:51) and fWwYqHhQ (SEQ ID NO:5). As shown in Table 1, such peptides have excellent activities in promoting generation of pre-beta HDL.

IV. Synthesis of Anti-Atherosclerotic Cyclic Peptides and Derivatives

The anti-atherosclerotic cyclic peptides suitable for the invention may be produced by any conventional automated or manual peptide synthesis methods. General principles and techniques for automated peptide synthesis are well known to those of skill in the art. Exemplified protocols of solid phase synthesis are detailed in Example 5 below. In some embodiments, the isolated, purified peptides or variants of the invention can be synthesized in vitro, e.g., by the solid phase peptide synthetic method or by enzyme catalyzed peptide synthesis or with the aid of recombinant DNA technology. Solid phase peptide synthetic method is an established and widely used method, which is described in references such as the following: Stewart et al., *Solid Phase Peptide Synthesis*, W. H. Freeman Co., San Francisco (1969); Merrifield, *J. Am. Chem. Soc.* 85 2149 (1963); Meienhofer in "Hormonal Proteins and Peptides," ed.; C. H. Li, Vol. 2 (Academic Press, 1973), pp. 48-267; and Bavaay and Merrifield, "The Peptides," eds. E. Gross and F. Meienhofer, Vol. 2 (Academic Press, 1980) pp. 3-285. Various automatic synthesizers are commercially available and can be used in accordance with known protocols. The synthesized peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography; or crystallization or precipitation from non-polar solvent or nonpolar/polar solvent mixtures. Purification by crystallization or precipitation is preferred.

To identify highly active cyclic peptides that have little or no undesired toxicity for mammalian cells, individual cyclic peptides, or libraries of cyclic peptides can be made and the individual cyclic peptides or cyclic peptides from those libraries can be screened for anti-atherosclerotic activity and toxicity using assays and techniques known in the art. For example, libraries of peptides can be made using a one-bead-one-compound strategy provided by Lam et al. (97 Chem. Rev. 411-448 (1997) or synthesized on macrobeads by a split and pool method of Furka, et al. (37 Int. J. Pept. Prot. Res. 487-493 (1991)). Mass spectrometric sequence analysis techniques enable rapid identification of every peptide within a given library. See, Biemann, K. 193 Methods Enzymol. 455 (1990). In general, synthetic operations, including peptide cyclization, are performed on solid support to avoid laborious and difficult to automate solution-phase operations. Moreover, the final product of the synthesis regimen is generally sufficiently pure for biological assays without laborious purification procedures. Peptide yields from each synthesis can be sufficient for performing 50 to 100 assays. Rapid, automatic mass-spectrometry-based peptide sequence analysis can be performed to identify peptide sequences that have high activity and to discard peptide sequences with low activity.

The synthetic approach employed can provide individually separable and identifiable peptide sequences to avoid the use of combinatorial library mixtures and laborious deconvolution techniques. However, libraries of impure mixtures of peptides can also be generated for testing. Impure preparations of peptides can be used for quick screening of combinations of sequences. When a mixture of peptides shows activity, the peptides in the mixture can either be individually isolated and tested or pure peptides having sequences known to be present in the impure mixture can be individually prepared and tested.

In some embodiments, the cyclic peptides described herein (e.g., compounds shown in FIG. 1 and Table 1) can be modified via backbone alkylation to identify derivative or analog compounds with similar or improved properties. As exemplified for compound 1 (SEQ ID NO:1) and a methylated derivative of compound 1 (SEQ ID NO:46) in FIGS. 7 and 8 herein, the alkylated derivatives can be similarly effective as their parent compounds in preventing the development of atherosclerotic lesions. On the other hand, backbone alkylation in the cyclic D,L-alpha peptides may prevent the formation of nanotubes and also improve oral bioavailability of the peptides.

In some embodiments, salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N-acylation and O-acylation may be carried out together, if desired.

Acid addition salts of the peptide or variant peptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Employing the cyclic peptides exemplified herein, the invention provides methods of identifying for novel anti-atherosclerotic cyclic peptides, analogs or derivatives with improved properties. An important step in the drug discovery process is the selection of a suitable lead chemical template upon which to base a chemistry analog program. The process of identifying a lead chemical template for a given molecular target typically involves screening a large number of compounds (often more than 100,000) in a functional assay, selecting a subset based on some arbitrary activity threshold for testing in a secondary assay to confirm activity, and then assessing the remaining active compounds for suitability of chemical elaboration.

The cyclic peptides described herein, e.g., the compounds shown in FIG. 1 and Table 1, provide lead compounds to search for related compounds that have improved biological or pharmaceutical properties. The screening methods of the invention typically involve synthesizing analogs, derivatives or variants of a cyclic peptide. Often, a library of structural analogs of a given cyclic peptide is prepared for the screening. To synthesize analogs or derivatives based from the chemical backbones of these anti-atherosclerotic cyclic peptides, only routinely practiced methods of organic chemistry synthesis are required. For example, combinatorial libraries of chemical analogs of a known compound can be produced by the encoded synthetic libraries (ESL) method as described in WO 95/12608, WO 93/06121, WO 94/08051, WO 95/35503 and WO 95/30642. Exemplary methods for synthesizing analogs of various compounds are also described in, e.g., by Overman, *Organic Reactions*, Volumes 1-62, Wiley-Interscience (2003); Broom et al., Fed Proc. 45: 2779-83, 1986; Ben-Menahem et al., Recent Prog Horm Res. 54:271-88, 1999; Schramm et al., Annu. Rev. Biochem. 67: 693-720, 1998; Bolin et al., Biopolymers 37: 57-66, 1995; Karten et al., Endocr Rev. 7: 44-66, 1986; Ho et al., *Tactics of Organic Synthesis*, Wiley-Interscience; (1994); and Scheit et al., *Nucleotide Analogs: Synthesis and Biological Function*, John Wiley & Sons (1980).

Once candidate structural analogs of a lead anti-atherosclerotic cyclic peptide are synthesized, a functional assay is then performed to identify one of the analogs or derivatives that have an improved biological property relative to that of the cyclic peptide from which the analogs or variants are derived. In some embodiments, a function assay can be performed by assaying a candidate peptide's ability to promote cholesterol efflux from macrophage cells and remodeled mature high-density lipoprotein (HDL) particles into nascent lipid-poor HDLs. This can be performed both in vitro and in vivo, as exemplified in the Examples herein. In addition, improved anti-atherosclerotic activity of candidate peptides may also be examined by monitoring total plasma cholesterol levels of a lab animal (e.g., mouse) that has been administered with the candidate peptide, as demonstrated in the Examples herein.

In some embodiments, structural analog compounds of a cyclic peptide of the invention can be screened for improved pharmacokinetic properties, e.g., in vivo half life. Compounds with such improved properties can be more suitable for various therapeutic applications. Improved pharmaceutical properties of a cyclic peptide analog can be assayed using methods such as those described in, e.g., Remington: *The Science and Practice of Pharmacy*, Mack Publishing Co., 20$^{th}$ ed., 2000.

V. Therapeutic Applications of Anti-Atherosclerosis Cyclic Peptides

The cyclic peptides disclosed herein can be employed in various prophylactic or therapeutic applications for treating or preventing atherosclerosis or disorders mediated by or associated with atherosclerosis. Related applications entail the use of these peptides to reduce total cholesterol level, to reduce LDL level and/or VLDL level, or to enhance HDL level in a subject. Atherosclerosis is an underlying or contributing factor of many diseases or disorders. Atherosclerosis affects the entire artery tree, but mostly larger, high-pressure vessels such as the coronary, renal, femoral, cerebral, and carotid arteries. These are termed clinically silent because the person having the infarction does not notice the problem and does not seek medical help, or when they do, physicians do not recognize what has happened. The complications of advanced atherosclerosis are chronic, slowly progressive and cumulative. Most commonly, soft plaque suddenly ruptures (see vulnerable plaque), causing the formation of a thrombus that will rapidly slow or stop blood flow, leading to death of the tissues fed by the artery in approximately 5 minutes. This catastrophic event is called an infarction. One of the most common recognized scenarios is called coronary thrombosis of a coronary artery, causing myocardial infarction (a heart attack). The same process in an artery to the brain is commonly called stroke. Another common scenario in very advanced disease is claudication from insufficient blood supply to the legs, typically caused by a combination of both stenosis and aneurysmal segments narrowed with clots.

As described above, various cyclic peptides may be employed and/or modified for practicing the present invention. Examples of such peptides are described herein in the Examples below. In some preferred embodiments, cyclic peptides employed in the therapeutic methods of the invention have a sequence formula of c[B-J-U1-X-U2-Z] as described above. For example, many cyclic peptides noted in FIG. 1 herein may be employed in the practice of the invention. Specific examples of such cyclic peptides include c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[wLwZeQeK] (SEQ ID NO:7), c[wL-wKdNdK] (SEQ ID NO:8), c[wLwRdNdK] (SEQ ID NO:9), c[wLwKdQdK] (SEQ ID NO:10), c[wLwKeNeK] (SEQ ID NO:11), c[wLwHeNeK] (SEQ ID NO:12), c[wL-wOeQeO] (SEQ ID NO:13), and c[wLwOeNeO] (SEQ ID NO:19). Other examples of cyclic peptides suitable for the therapeutic applications of the inveniton include c[fWwY-qHhQ] (SEQ ID NO:5), c[wLwSeQhK] (SEQ ID NO:40), c[wLwKhShK] (SEQ ID NO:53), c[(Me)wLwR(Me)eQeR] (SEQ ID NO:46), c[WlWwkhkh] (SEQ ID NO:47), c[Wl-WrEqEr] (SEQ ID NO:50), c[fWwYtRhS] (SEQ ID NO:51), c[wFyYhOrS] (SEQ ID NO:48), c[(PA)wLlHsKk] (SEQ ID NO:49), c[wFfYrHhS] (SEQ ID NO:52), and c[WIWwKhKh] (SEQ ID NO:82). Additional cyclic peptides that can be employed in the practice of the invention are listed in Table 1.

Some embodiments of the invention are directed to using the anti-atherosclerotic cyclic peptides described herein to prevent/treat hypercholesterolemia, to upregulate HDL level, or to reduce plasma cholesterol level (e.g., by reducing LDL and/or VLDL level) in a subject. In some embodiments, the cyclic peptides of the invention are employed to prevent the development or to reverse the progression of other diseases associated with atherosclerosis, e.g., cardiovascular disorders. In some preferred embodiments, these therapeutic applications of the invention employ a cyclic peptide selected from c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[fWwYqHhQ] (SEQ ID NO:5), c[LwLwLrKe] (SEQ ID NO:6), c[wLwZeQeK] (SEQ ID NO:7), c[wLwKdNdK] (SEQ ID NO:8), c[wLwRdNdK] (SEQ ID NO:9), c[wLwKdQdK] (SEQ ID NO:10), c[wLwKeNeK] (SEQ ID NO:11), c[wLwHeNeK] (SEQ ID NO:12), c[wLwSeQhK] (SEQ ID NO:40), c[wLwKhShK] (SEQ ID NO:53), c[(Me)wLwR(Me)eQeR] (SEQ ID NO:46), c[WlWwkhkh] (SEQ ID NO:47), and c[WIWrEqEr] (SEQ ID NO:50), c[fWwYtRhS] (SEQ ID NO:51), c[wFyYhOrS] (SEQ ID NO:48), c[(PA)wLlHsKk] (SEQ ID NO:49), c[wFfYrHhS] (SEQ ID NO:52), and c[WIWwKhKh] (SEQ ID NO:82). As demonstrated in the Examples below, these compounds are capable of substantially reducing total plasma cholesterol levels (reducing LDL/VLDL levels), promoting generation of HDL, and inhibiting the development of atherosclerotic lesions.

Typically, the therapeutic or prophylactic methods of the invention entail administrating to a subject in need of treatment with an anti-atherosclerotic cyclic peptide of the invention (e.g., Compounds 1 or 4 shown in FIG. 1). The method according to the present invention can be administered to a subject which has been diagnosed with any diseases or disorders that are mediated by or associated with atherosclerosis. These can be any coronary disorder or vascular disorders including atherosclerotic vascular disease, such as aneurysm or stroke, asymptomatic coronary artery diseases, chronic ischemic disorders without myocardial necrosis, such as stable or effort angina pectoris; acute ischemic disorders with myocardial necrosis, such as unstable angina pectoris; and ischemic disorders such as myocardial infarction.

The anti-atherosclerotic cyclic peptide of the invention may be administered in the form of a pharmaceutical composition. As detailed below, a pharmaceutical composition contains a therapeutically effective amount of the anti-atherosclerotic cyclic peptide. In addition to the anti-atherosclerotic cyclic peptide, the pharmaceutical composition typically also contains a pharmaceutically acceptable carrier or excipient.

In order to better treat atherosclerosis or to inhibit progression of atherosclerosis, the anti-atherosclerotic cyclic peptides can be used in conjunction with other known drugs that can slow buildup of atherosclerotic plaque buildup, e.g., CRESTOR® (rosuvastatin calcium). The anti-atherosclerotic cyclic peptides of the invention may also be combined with other therapeutic agents useful in the treatment of other cardiovascular or metabolic disorders such as hypertension, hyperlipidaemias, dyslipidaemias, diabetes, and in any condition where enhancement of reverse cholesterol transport and/or improvement of LDL:HDL ratios would be of potential clinical benefit. Examples of such therapies include inhibitors of 3-hydroxy-3-methyl-glutaryl-CoA reductase (HMG CoA reductase) (e.g. atorvastatin, pravastatin, simvastatin, lovastatin, rosuvastatin and others), cholesterol absorption inhibitors (e.g. ezetimibe), bile sequestrants (e.g., cholestyramine), microsomal triglyceride transfer protein (MTP) inhibitors, peroxisome proliferator-activated receptor modulators (e.g., muraglitazar, rosiglitazone, fibrates and others), cholesterol ester transfer protein inhibitors, nicotinic acid derivatives (e.g., Niaspan), Acyl coenzyme A: cholesterol acyl transferase (ACAT) inhibitors (e.g., eflucimibe), farnesoid X receptor modulators, therapies used for the treatment of metabolic syndrome or type 2 diabetes (e.g. metformin). Compounds of the invention may be combined with anti-inflammatory therapies (e.g. aspirin) and with treatments for neurodegenerative diseases (e.g., Aricept®, Exelon®, Reminyl®, and Ebixa®).

VI. Pharmaceutical Combinations and Methods of Administration

The anti-atherosclerotic cyclic peptides (e.g., compounds shown in FIG. 1 and Table 1) and the other therapeutic agents disclosed herein can be administered directly to subjects in need of treatment. However, these therapeutic compounds are preferably administered to the subjects in pharmaceutical compositions which comprise the cyclic peptide and/or other active agents along with a pharmaceutically acceptable carrier, diluent or excipient in unit dosage form. Accordingly, the invention provides pharmaceutical compositions comprising one or more of the anti-atherosclerotic cyclic peptides disclosed herein. The invention also provides a use of these cyclic peptides in the preparation of pharmaceutical compositions or medicaments for treating or preventing the above described diseases or medical disorders that are mediated by or associated with atherosclerosis.

Pharmaceutically acceptable carriers are agents which are not biologically or otherwise undesirable. These agents can be administered to a subject along with an anti-atherosclerotic cyclic peptide without causing any undesirable biological effects or interacting in a deleterious manner with any of the components of the pharmaceutical composition. The compositions can additionally contain other therapeutic agents that are suitable for treating or preventing atherosclerosis or ameliorating related symptoms (e.g., cholesterol reducing agents). Pharmaceutically carriers enhance or stabilize the composition or facilitate preparation of the composition. Pharmaceutically acceptable carriers include solvents, dispersion media, coatings, antibacterial and antifungal agents, isotonic and absorption delaying agents, and the like that are physiologically compatible. The pharmaceutically acceptable carrier employed should be suitable for various routes of administration described herein. Additional guidance for selecting appropriate pharmaceutically acceptable carriers is provided in the art, e.g., Remington: *The Science and Practice of Pharmacy*, Mack Publishing Co., $20^{th}$ ed., 2000.

A pharmaceutical composition containing an anti-atherosclerotic cyclic peptide described herein and/or other therapeutic agents can be administered by a variety of methods known in the art, e.g., oral administration as exemplified in the Examples below. The routes and/or modes of administration vary depending upon the desired results. Depending on the route of administration, the active therapeutic agent may be coated in a material to protect the compound from the action of acids and other natural conditions that may inactivate the agent. Conventional pharmaceutical practice may be employed to provide suitable formulations to administer such compositions to subjects. Any appropriate route of administration may be employed. These include, but are not limited to, oral, intravenous, parenteral, transcutaneous, subcutaneous, intraperitoneal, intramuscular, intracranial, intraorbital, intraventricular, intracapsular, and intraspinal administration. Depending on the specific conditions of the subject to be treated, either systemic or localized delivery of the therapeutic agents may be used in the treatment.

In some embodiments, local administration of cyclic peptides may be desired in order to achieve the intended therapeutic effect. Many methods of localized delivery of therapeutic agents or formulations can be used in the practice of the invention. For example, local administration of a cyclic peptide to the desired cardiac muscle in a subject can be accomplished by a percutaneous route, by therapeutic cardiac catheterization, by intrapericardial injection or infusion, or by direct intracardiac muscle injection. Suitable methods also include any other routes which allow the therapeutic agent to be applied locally to the heart. For example, the therapeutic agent may be applied from the blood stream, by being placed directly in the heart through the coronary arteries or veins onto the heart surface, or through the ventricular or atrial walls and onto the heart surface. The therapeutic agent may also be applied through direct application during extensive surgical field exposure, or through direct application during minimally invasive exposure, e.g., through a pericardial window or heart port.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, e.g., polyoxyethylene-9-lauryl ether, glycocholate and deoxycholate, or may be oily solutions for administration in the form of nasal drops, or as a gel.

The cyclic peptides for use in the methods of the invention should be administered to a subject in an amount that is sufficient to achieve the desired therapeutic effect (e.g., eliminating or ameliorating symptoms associated with undesired immune responses) in a subject in need thereof. Typically, a therapeutically effective dose or efficacious dose of the cyclic peptide is employed in the pharmaceutical compositions of the invention. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular compositions of the present invention employed, the route of administration, the time of administration, and the rate of excretion of the particular compound being employed. It also depends on the duration of the treatment, other drugs, compounds and/or materials used in combination with the particular compositions employed, the age, gender, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Typically, a pharmaceutically effective dosage would be between about 0.001 and 100 mg/kg body weight of the subject to be treated.

The anti-atherosclerotic cyclic peptides and other therapeutic regimens described herein are usually administered to the subjects on multiple occasions. Intervals between single dosages can be daily, weekly, monthly or yearly. Intervals can also be irregular as indicated by measuring blood levels of the anti-atherosclerotic cyclic peptides and the other therapeutic agents used in the subject. In some methods, dosage is adjusted to achieve a plasma compound concentration of 1-1000 µg/ml, and in some methods 25-300 µg/ml or 10-100 µg/ml. Alternatively, the therapeutic agents can be administered as a sustained release formulation, in which case less frequent administration is required. Dosage and frequency vary depending on the half-life of the anti-atherosclerotic cyclic peptide and the other drugs in the subject. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

In some related embodiments, the present invention provides a packaged pharmaceutical composition for treating or preventing atherosclerosis such as a kit or other container. The kit or container holds a therapeutically effective amount of a pharmaceutical composition for treating atherosclerosis and optionally also an instruction sheet detailing how to use the pharmaceutical composition for treating atherosclerosis or other diseases mediated by or associated with atherosclerosis. The pharmaceutical composition in the kit contains at least one cyclic peptide of the present invention, in a therapeutically effective amount such that atherosclerosis is treated.

EXAMPLES

The following examples are provided to further illustrate the invention but not to limit its scope. Other variants of the invention will be readily apparent to one of ordinary skill in the art and are encompassed by the appended claims.

Example 1 Design, Synthesis, and Screening of Cyclic d,l-α-Peptides

We carried out several iterations of peptide design, synthesis, and screening. In general, some of the peptide sequences (as shown in FIG. 1) were designed to bear a charge distribution similar to that found in class A α-helices, which characterize plasma apolipoproteins. Class A α-helices have an amphiphilic structure in which the cationic residues are clustered at the polar/nonpolar interface and the anionic residues are near the center of the polar region.

Therefore, the cyclic D,L-α-peptides in our panel generally contain cationic Arg, Lys, Orn (O), diaminobutyric acid, or diaminopropionic acid residues near the polar/nonpolar interface, and negatively charged Asp or Glu residues at the center of the polar face (FIG. 1). The likely mechanism of action of the cyclic D,L-α-peptides involves membrane insertion and peptide self-assembly into nanotubular complexes, whereas conventional apoA-I mimetic peptides fold into an α-helix to function within the membrane.

Example 2 Plasma HDL Remodeling and Promotion of Cholesterol Efflux

As an initial phase of investigation, we evaluated in vitro the effectiveness of our cyclic D,L-α-peptides to remodel mature human plasma HDLs into lipid-poor HDL (FIG. 1 and FIG. 2a). Lipid-poor HDL particles are key acceptors of cholesterol in reverse cholesterol transport and are thus crucial for combating atherosclerosis. In fact, with respect to the cholesterol efflux capacity of human sera, the levels of lipid-poor HDL correlate much better than the levels of HDL-cholesterol or apoA-I. Briefly, our assay involved incubating human plasma with a peptide, after which the plasma sample was subjected to non-denaturing gradient gel electrophoresis (NDGGE) to separate the HDL subspecies and then immunoblotted for human apoA-I. The ranked activities of the cyclic D,L-α-peptides in promoting formation of lipid-poor HDL are shown in FIG. 1. It should be noted that there are inherent variabilities associated with electrophoretic transfer, staining, and densitometric quantitation, so the peptide ranking should be viewed as an approximate guide to relative plasma HDL remodeling efficacy. Nevertheless, the rankings were similar overall whether the panel was assayed by using peptide stock solutions prepared in 10% sucrose/$H_2O$ (FIGS. 1 and 2a) or peptide stock solutions prepared in 1:1 DMSO/$H_2O$. From these preliminary structure-activity relationship (SAR) studies, we identified a pronounced sequence dependence for efficient plasma HDL remodeling (vide infra).

Selected cyclic D,L-α-peptides were further evaluated for their ability to promote cellular cholesterol efflux from mouse macrophage J774 cells. A main factor for HDL anti-atherogenicity is its role in reverse cholesterol transport, of which cellular cholesterol efflux is a critical component. To measure efflux mediated by the cyclic D,L-α-peptides, cholesterol-laden cells were incubated with peptide-treated plasma for 4 h, after which the level of cholesterol effluxed to the media was measured as described in Sankaranarayanan et al., J. Lipid Res. 52, 2332-2340, 2011. The cyclic D,L-α-peptides markedly promoted cholesterol efflux compared to the vehicle control, and peptide 1 showed a clear concentration dependency (FIG. 2b). The cyclic D,L-α-peptides 1 and 4 were only marginally less effective than the α-helical apoA-I mimetic 4F in promoting cholesterol efflux at the same mg/mL concentration, and did not appear to be toxic based on the cellular morphology and density.

Example 3 Structure—Activity Relationships

Inspection of the active cyclic D,L-α-peptides indicates that they have an amphiphilic topology with a hydrophobic Trp-Leu-Trp (wLw) segment and a positively charged or neutral Ser residue adjacent to the hydrophobic face. Each active compound contains an Asn or Gln residue in the center of the polar face, flanked by negatively charged or Ser residues. The observed charge distribution was necessary, but not sufficient, for plasma remodeling activity. Subtle amino acid changes in either the hydrophilic or the hydrophobic face dramatically impacted the HDL remodeling efficiency of the cyclic D,L-α-peptides. For example, compare the difference in activity of c[wLwSeQsO] (SEQ ID NO:4) and c[wLwSeQsK] (SEQ ID NO:30) or c[wLwZeQeK] (SEQ ID NO:7) and c[wLwHeQeK] (SEQ ID NO:44) (Z=diaminopropionic acid) (FIG. 1). Likewise, c[wLwReQeR] (SEQ ID NO:1) was considerably more active than any of four analogs designed to be more hydrophobic by replacing the Leu residue with naphthylalanine (Nal) (compound 28), homoleucine (compound 29), 2-amino-octanoic acid (Aoc) (compound 31), or Trp (compound 41) (FIG. 1). These observations are consistent with our previous studies with membrane active antimicrobial cyclic peptide nanotubes, where seemingly small differences in amino acid sequence at the peptide monomer level were greatly amplified through peptide self-assembly into nanotubes and the expansion into multivalent side chain presentation. Finally, we prepared and assayed peptide c[wLwErQrE] (SEQ ID NO:37), in which the pattern of charged residues is swapped compared to that in compound 1 (and the other active sequences) by placing the anionic residues at the polar/nonpolar interface. Notably, the plasma HDL remodeling and cholesterol efflux activities of compound 37 were dramatically reduced compared to that of compound 1 (FIGS. 1 and 2b), despite having the same amino acids; this supported the identified charge distribution as functionally important.

Figure 2:
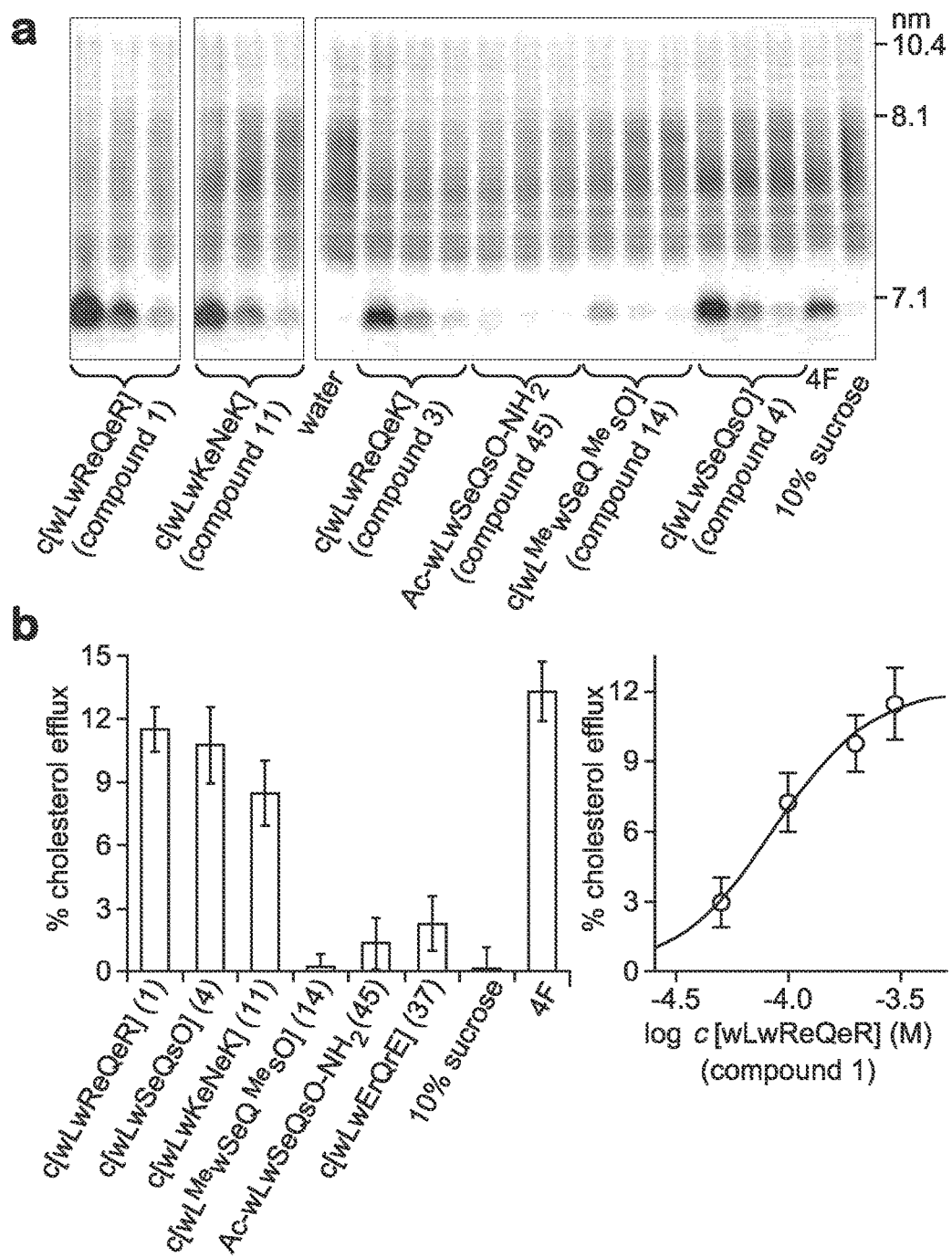
FIGS. 2A-2B show cyclic D,L-α-peptides promote plasma HDL remodeling and cholesterol efflux in vitro. (A) Selected cyclic D,L-α-peptides enriched the level of lipid-poor HDL by remodeling human plasma HDL particles. The peptide compounds used are Compounds 1 (SEQ ID NO:1), 11 (SEQ ID NO:11), 3 (SEQ ID NO:3), 45 (SEQ ID NO:45), 14 (SEQ ID NO:14) and 4 (SEQ ID NO:4). The peptides were assayed at 0.4, 0.2, and 0.1 mg/mL (~360, 180, and 90 µM). Peptide 4F was used as a positive control at 0.1 mg/mL (43 µM). The "water" and "10% sucrose" lanes are negative controls. Lipid-poor HDL (~7 nm in size) are key initial acceptors of cholesterol in reverse cholesterol transport. "O" denotes ornithine. (B) Selected cyclic D,L-α-peptides promoted cellular cholesterol efflux in vitro. Compound numbers and their SEQ ID NOs, which are identical for each compound, are shown in the parentheses after each of the compound sequence in the figure. All compounds in the left panel were assayed at 0.3 mg/mL (~270 µM cyclic peptide) in human plasma. Efflux was measured from mouse macrophage J774 cells incubated with 2% apoB-depleted plasma samples for 4 h. Values are shown as mean±SD of samples in quadruplicate, and are given relative to the vehicle-treated plasma sample as 0% efflux.

To gain further insight into the mechanistic features required for the observed apoA-I mimetic properties, we synthesized and assayed several derivatives of the active cyclic D,L-α-peptides. We established that the cyclic structure was required for activity by preparing acetylated linear peptide Ac-wLwSeQsO-$NH_2$ (SEQ ID NO:45), which failed to remodel plasma HDL or promote cholesterol efflux (FIGS. 2a and 2b) even though it retains amphiphilicity. Likewise, we also examined whether peptide self-assembly is required for activity by preparing cyclic backbone N-methylated analog c[wL$^{Me}$wSeQ$^{Me}$sO] (SEQ ID NO:14). Such backbone methylations limit peptide self-assembly to dimeric complexes, as opposed to stacks within nanotubes, by rendering one face of the peptide incapable of intersubunit hydrogen bonding. As shown in FIG. 2, the efficacy of 14 in plasma remodeling and cholesterol efflux was greatly diminished compared to the unmethylated parent, compound 4. Together, these studies support a mechanism involving self-assembly of cyclic peptides into supramolecular nanotube species.

Example 4 In Vivo Efficacy Studies

Figure 3:
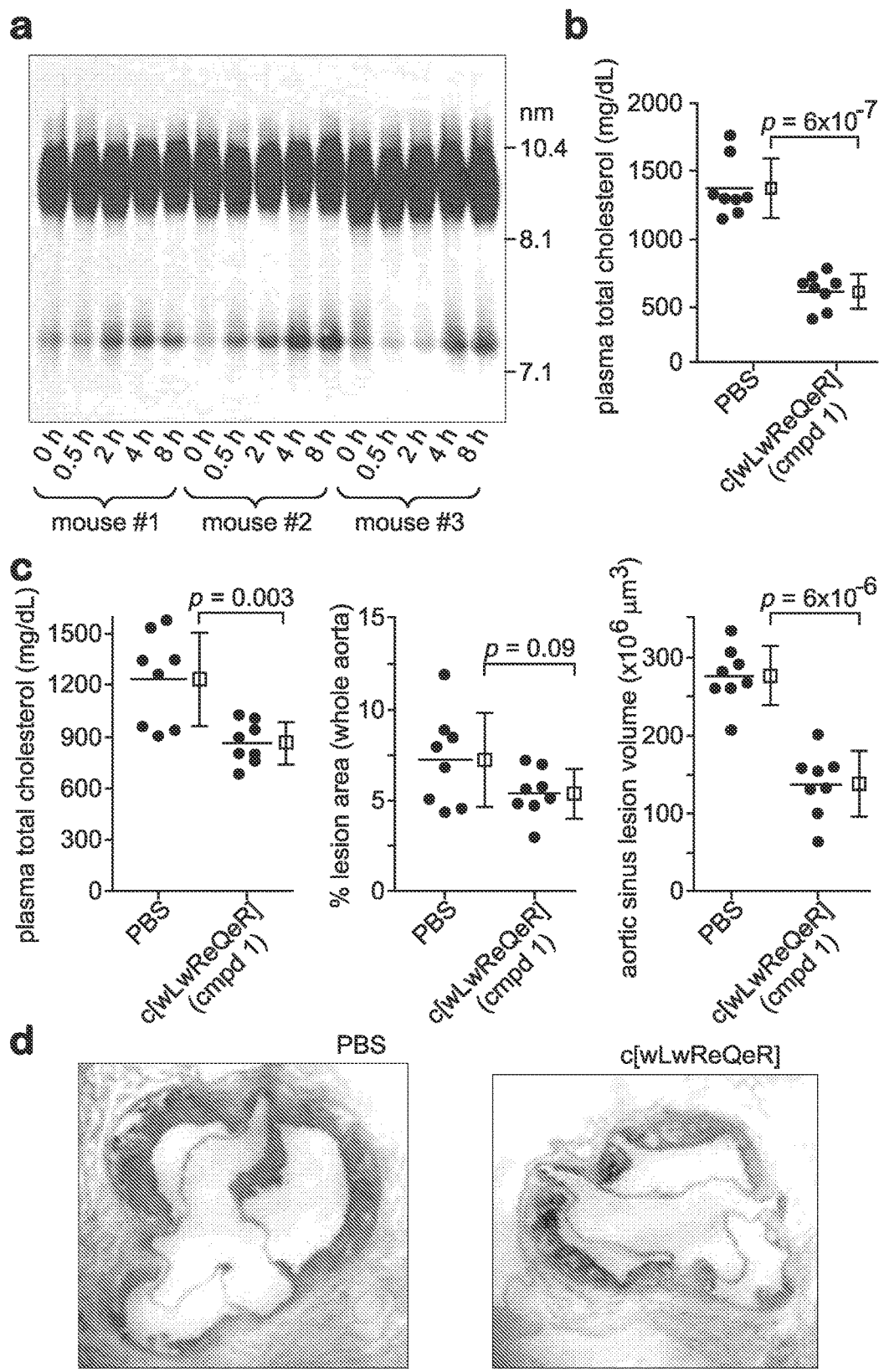
FIGS. 3A-3D show that, in vivo, cyclic D,L-α-peptide 1 (SEQ ID NO:1) remodels plasma HDL, reduces plasma cholesterol, and prevents the development of atherosclerotic lesions. (A) Peptide 1 increased the level of lipid-poor HDL (~7.3 nm) after intraperitoneal injection (20 mg/kg) to male BALB/c mice (n=3), as determined by Western blotting for mouse apoA-I. (B) In a 2-week pilot study, peptide 1 administered orally reduced total plasma cholesterol by 55% compared to vehicle controls. Female LDLr-null mice maintained on a high-fat diet were administered the peptide in 1% sucrose/PBS (n=8) or 1% sucrose/PBS alone (n=8), as the drinking water ad libitum. The daily dose of peptide per mouse was ~0.5 mg (~25 mg/kg/day). (C, D) After 10 weeks of oral administration in drinking water ad libitum to female high-fat-fed LDLr-null mice, peptide 1 was found to reduce total plasma cholesterol, whole aorta lesion area, and aortic sinus lesion volume (see panel d for representative aortic sinus images). All plots are shown as a scatter plot along with mean±SD. p values were determined by a Student's unpaired two-tailed t-test.
Figure 4:
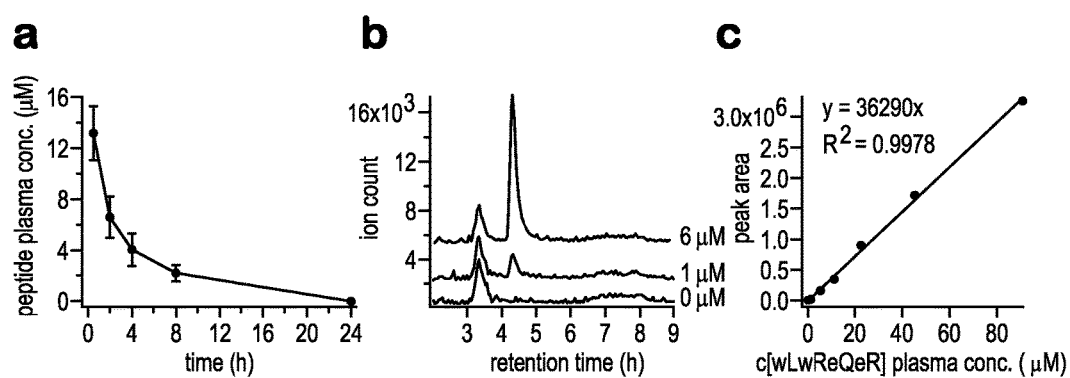
FIGS. 4A-4C show pharmacokinetics of cyclic D,L-α-peptide c[wLwReQeR] (peptide 1; SEQ ID NO:1) in mice, as determined by using HPLC/MS SIM. (A) Pharmacokinetic profile for the peptide in male BALB/c mice (n=3) after an i.p. dose of 16 mg/kg. Data are given as mean±SD. (B) Representative MS selected ion trace for ion 592.8 ([M+2H]2+) at cyclic peptide concentrations of 0 µM, 1 µM (lower limit of detection), and 6 µM in mouse plasma. The peak at 4.4 min corresponds to the cyclic peptide. (C) Representative calibration curve of cyclic peptide in mouse plasma.

To ascertain if the cyclic D,L-α-peptides function in vivo as modulators of HDL, we administered 1 to mice (BALB/c, n=3) via intraperitoneal injection (i.p.) at a dose of 20 mg/kg. After various times, blood was drawn and the plasma was analyzed by Western blotting to determine the levels of the HDL subpopulations. We observed in each mouse a marked increase in the amount of lipid-poor HDL for up to 8 h from the pre-injection time point (FIG. 3a), consistent with the in vitro assay with human plasma. A pharmacokinetic study of compound 1 in mice (BALB/c, n=3) with i.p. administration revealed that this peptide has a plasma half-life of ~2 h (FIG. 4).

Figure 5:
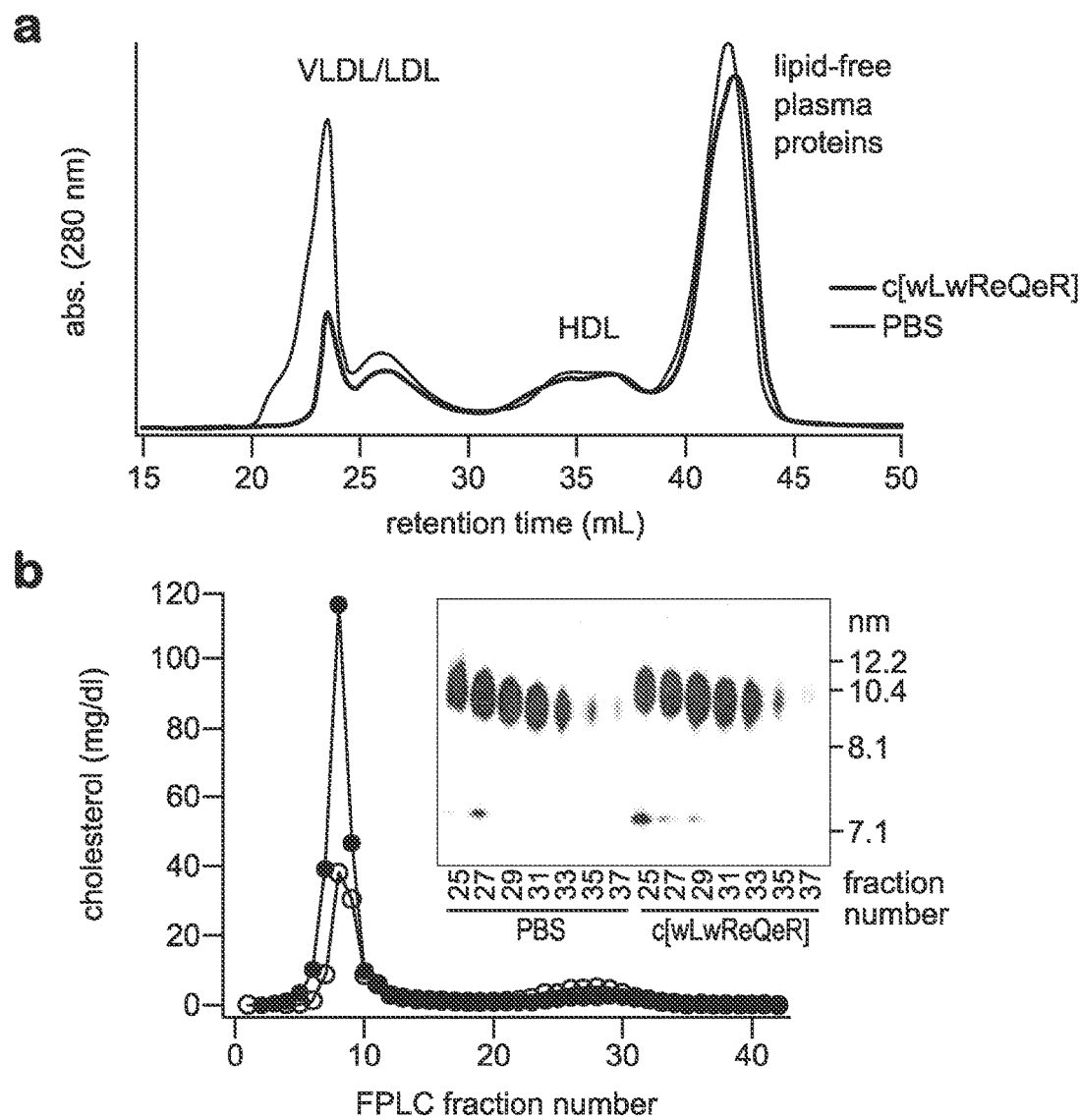
FIGS. 5A-5B show lipoprotein profile analyses for LDLr-/- mice treated for two weeks with vehicle or oral (drinking water) cyclic D,L-α-peptide c[wLwReQeR] (SEQ ID NO:1) (high dose, ~25 mg/kg/day). (A) Pooled plasma from the eight mice in each group was fractionated via FPLC. The resulting lipoprotein profile indicated that the majority of total cholesterol reductions observed for the cyclic peptide group are due to decreases in the VLDL and LDL levels. Although HDL levels are comparable for both groups, the HDL particles in the cyclic peptide-treated group have undergone a modest shift to smaller (later eluting) particles compared to PBS control. (B) The cholesterol level in each fraction from the FPLC fractionation was measured, confirming that the reductions in plasma total cholesterol stem largely from reduced VLDL. The inset shows a western blot (blotted for mouse apoA-I) of selected fractions from the HDL region of the fractionation.

Encouraged by the above findings, we carried out a 2-week pilot study to determine the effect of 1 on plasma total cholesterol levels. As an animal model, we employed the LDLr-null mouse, which has a human-like lipoprotein profile and is a leading animal model for studying hypercholesterolemia and atherogenesis. Considering that the abiotic nature of cyclic D,L-α-peptides renders them highly resistant to proteolysis, we chose to conduct this pilot in vivo efficacy study via the more convenient oral route of administration. Thus, the cyclic D,L-α-peptide was administered orally in the drinking water for two weeks (each mouse drank ~0.5 mg peptide per day, or ~25 mg/kg/day) to mice maintained on a high-fat diet. After the two weeks, the peptide-treated animals (n=8) exhibited a 55% reduction in total plasma cholesterol compared to control animals (n=8) (FIG. 3b). As determined by FPLC fractionation of pooled plasma samples, the reductions in plasma total cholesterol stemmed mainly from reduced levels of VLDL and LDL (FIG. 5). However, encouragingly, the plasma HDLs were also remodeled in favor of the smaller HDL particle sizes (FIG. 5).

Figure 6:
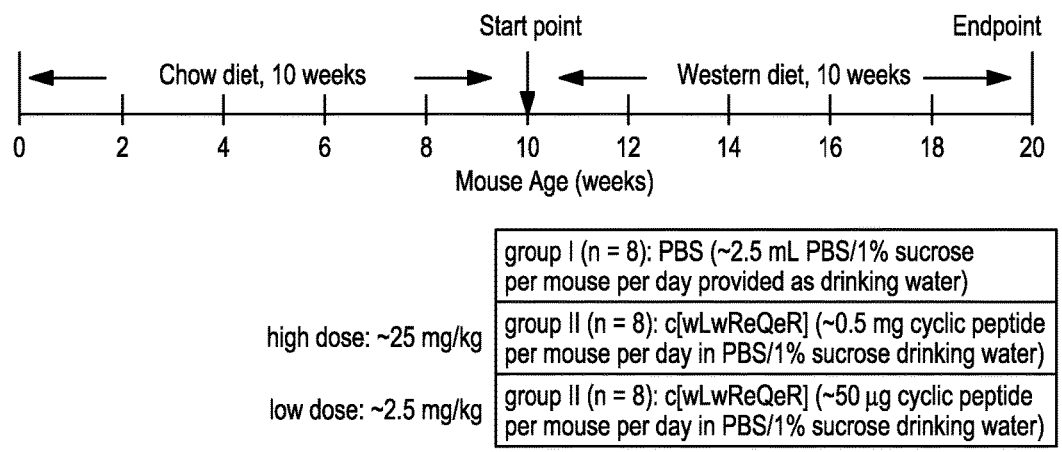
FIG. 6 shows feeding and cyclic D,L-α-peptide treatment schedule. Female LDLr-/- mice were divided into 3 groups (8 mice per group). Group I, as vehicle control, received PBS containing 1% sucrose; groups II and III received high dose (~25 mg/kg/day) and low dose (~2.5 mg/kg/day) cyclic peptide c[wLwReQeR] (SEQ ID NO:1), respectively, in PBS containing 1% sucrose as their drinking water for 10 weeks.

We continued oral administration of the peptide to the animals for an additional eight weeks (ten weeks total for the study) to determine how the peptide would impact the development of atherosclerotic lesions (see FIG. 6 for treatment schedule). At the completion of the 10-week study, the total plasma cholesterol level in the peptide-treated animals was 30% lower than in control animals (FIG. 2c). Moreover, an analysis of the whole aorta lesion area and the aortic sinus lesion volume indicated reductions in atherosclerotic lesions of 26% and 50%, respectively (FIGS. 2c, d). No differences were observed between the groups in terms of body weight, liver weight, spleen weight, food or water intake, or the liver enzymes ALT and AST. When administered orally in the drinking water at 25 mg/kg/day, the plasma concentration of compound 1 was below the 1 µM limit of detection (data not shown). In a follow-up, 10-week study using a 10-fold lower dose of compound 1 (~2.5 mg/kg/day/mouse), again administered in the drinking water, the treated animals (n=8) showed a 17% reduction in plasma cholesterol levels compared to control animals (n=8) after two weeks, but at the completion of the 10-week study there were no significant differences in plasma cholesterol or atherosclerotic lesion results.

Example 5 Experimental Procedures and Other Studies

This Example describes some additional studies and the experimental procedures and materials employed in the studies detailed herein.

Abbreviations: BODIPY, boron-dipyrromethene; Cpt-cAMP, 8-(4-chlorophenylthio)-adenosine-3',5'-cyclic monophosphate; DIC, 1,3-diisopropylcarbodiimide; Dmab, 4-{N-[1-(4,4-dimethyl-2,6-dioxocyclohexylidene)-3-methylbutyl]-amino}benzyl; DMEM, Dulbecco's Modified Eagle Medium; DMF, dimethylformamide; DMSO, dimethylsulfoxide; EDTA, ethylendiamine-N,N,N'N',-tetraacetic acid; FBS, fetal bovine serum; HRP, horseradish peroxidase; LPDS, lipoprotein-deficient serum; MBHA, 4-methylbenzhydrylamine; MEM, Minimum Essential Medium Eagle; NDGGE, nondenaturating gradient gel electrophoresis; NMP, N-methylpyrrolidin-2-one; PBS, phosphate-buffered saline; PEG, polyethylene glycol; PyBroP, Bromo-tris-pyrrolidino phosphoniumhexafluorophosphate; TBS, tris-buffered saline; TBST, tris-buffered-saline+0.1% Tween20; TFA, trifluoroacetic acid; TIS, triisopropylsilane; tris, tris (hydroxymethyl)aminomethane; Trt, trityl; TSRI, The Scripps Research Institute.

Materials: Unless otherwise noted, chemicals were purchased from Sigma-Aldrich or Fisher Scientific. Amino acids, Rink amide MBHA resin, and N-hydroxybenzotriazole (HOBt) were purchased from Aapptec or NovaBiochem. Trifluoroacetic acid (TFA) was obtained from Halocarbon Products (Hackensack, N.J.). MEM buffered with 10 mM HEPES (MEM-HEPES) was prepared using HEPES (pH 7.4, 1 M) purchased from Life Technologies. BODIPY-cholesterol was purchased from Avanti Polar Lipids, Inc. (Birmingham, Ala.). Polyethylene glycol 8,000 (50% w/v) was purchased from Hampton Research. Methyl-β-cyclodextrin, Sandoz, lipoprotein-deficient serum (LPDS), and 8-(4-chlorophenylthio)-adenosine-3',5'-cyclic monophosphate (Cpt-cAMP) were purchased from Sigma-Aldrich. HRP-conjugated goat anti-human apoA-I antibody was from Academy Bio-Medical (#11H-Gla), rabbit anti-mouse apoA-I antibody was from Meridian Life Science, and HRP-conjugated anti-rabbit IgG was from Thermo. Human plasma was obtained from normal healthy donors through the TSRI Normal Blood Donor Program. Mice were bred inhouse (LDLr-null) or were obtained from the TSRI Department of Animal Resources.

Solid-phase peptide synthesis (SPPS): Peptides were synthesized by using standard Fmoc chemistry with an Advanced Chemtech Apex 396 peptide synthesizer. A typical synthesis was performed on 0.09-mmol scale using 0.6 mmol/g Rink amide MBHA resin (Novabiochem) loaded with Fmoc-Glu-ODmab or Fmoc-Glu-OAll via the side chain to yield a Gln residue after cleavage from the resin. For sequences not containing a glutamine residue for side chain attachment, an asparagine or lysine side chain was used for anchoring to the resin during solid phase synthesis. Standard side chain protecting groups included Gln(Trt), Asn(Trt), Lys(Boc), Orn(Boc), diaminopropionic acid(Boc), diaminobutyric acid(Boc), His(Trt), Ser(tBu), Trp(Boc), Glu (OtBu). Chain elongations were achieved using DIC and HOBt in NMP with 90-min couplings. Fmoc deprotection was achieved using 25% piperidine in NMP. After full elongation of the peptide, the terminal Fmoc was removed, and then the Dmab or All group was cleaved using 2% hydrazine in DMF (3×5 min) or Pd(PPh$_3$)$_4$ with PhSiH$_3$ in CH$_2$Cl$_2$, respectively. The peptides were cyclized on resin using PyAoP (5 mol-equiv) and iPr$_2$NEt (12 mol-equiv) in DMF for 12 h. Peptides were cleaved from the resin with concomitant side chain deprotection by agitation in a solution of 95:2.5:2.5 TFA/TIS/water for 3 h. The peptide was precipitated with ether, centrifuged, and washed three additional times with ether. The crude peptides were purified by preparative reverse-phase (RP)-HPLC on a Vydac 218TP C18 or 214TP C4 column. Purity was confirmed by analytical RP-HPLC. Purified peptides were characterized by analytical HPLC and MALDI-TOF mass spectrometry. Analytical RP-HPLC was performed using a Vydac 214TP C-4 column or a Zorbax 300-SB C-18 column connected to a Hitachi D-7000 HPLC system. Binary gradients of solvent A (99% H$_2$O, 0.9% acetonitrile, 0.1% TFA) and solvent B (90% acetonitrile, 9.9% H$_2$O, 0.07% TFA) were employed for HPLC.

The N-methylated derivative of peptide 14, c[wL$^{Me}$wS-eQ$^{Me}$sO], was prepared by loading a 2-chlorotrityl chloride resin with Fmoc-Ser-OAll via the side chain. The peptide synthesis proceeded through the Gln residue, using Fmoc-MeLeu-OH (NovaBiochem). The amine of the Gln residue was methylated selectively on the solid support following the method of Biron et al. (J. Pept. Sci. 12, 213-219, 2006). The synthesis then continued as described above. Coupling reactions to methylated amine groups were carried out using PyBroP (5 mol-equiv) and iPr$_2$NEt (12 mol-equiv) in DMF for 12 h.

Human plasma remodeling: All procedures involving human samples were approved by TSRI Institutional Review Board. Procedures were modified from those reported in Troutt et al., J. Lipid Res. 49, 581-587, 2008. Blood samples from normal healthy human donors were obtained from TSRI Normal Blood Donor Program. EDTA-anticoagulated whole blood was centrifuged at 1500×g for 15 min within 1 h of being drawn from the donor. The plasma layer was aliquoted and used immediately or frozen at −80° C. for future use. Peptide stock solutions were prepared at ~15 mM peptide in 50% DMSO for initial screenings, or at ~2 mM peptide in 10% sucrose for remodeling assays at lower concentrations (FIG. 1) and cholesterol efflux assays (FIG. 2). Plasma samples (30 µL) were treated with peptide stocks, and the samples were incubated at 37° C. for 0.5-1 h, and then quenched by adding 270 µL of 50% sucrose (1:9 dilution). Samples were mixed with 6× native loading buffer (125 mM tris, pH 6.8, 0.02% bromophenol, 20% glycerol), of which 6 µL was loaded onto a 4-20% polyacrylamide gel. The molecular weight ladder used was High Molecular Weight Calibration Kit (Amersham Biosciences, #17-0445-01). Gels were run at constant 80 V at 4° C. for 14 h using a Laemli buffer system (25 mM tris, 192 mM glycine, pH 8.3). Gels were then blotted onto nitrocellulose membranes (0.45 µm, Bio-Rad) at constant 30 V at 4° C. for 2 h using the Laemli buffer (no methanol). The membrane was blocked with 3% BSA in TBS (20 mM tris, 150 mM NaCl, pH 7.6) for 1 h at 23° C., and then washed once for 10 min with TBST (20 mM tris, 150 mM NaCl, pH 7.6, 0.1% tween-20). The membrane was next incubated with 3% BSA in TBST containing a ~1:8000 dilution of HRP-conjugated goat anti-human apoA-I antibody (Academy Bio-Medical, #11H-Gla) for 1 h at 23° C. The membrane was extensively washed with TBST (at least 6×10 min) and once with TBS. The membrane was incubated with ECL reagent (Thermo SuperSignal West Pico) for 5 min, and then exposed to photographic film (Kodak BioMax Light). The films were scanned and quantified by densitometry using the program LabWorks (v. 4.0.0.8). The data from individual blots were normalized by scaling the densitometry values using a "no-treatment" sample and a 4F (215 µM) sample from each individual blot as the low and high signals, respectively.

Cholesterol Efflux

Preparation of labeling medium: These procedures were modified from that reported in Sankaranarayanan et al., J. Lipid Res. 52, 2332-2340, 2011. The labeling medium was prepared by complexing the unlabeled cholesterol and BODIPY-cholesterol (20% of the total cholesterol) with methyl-β-cyclodextrin (CD) at a molar ratio of 1:40 (total cholesterol/CD). Unlabeled cholesterol and BODIPY-cholesterol were dissolved in chloroform and dried in a round bottom flask by rotor-evaporation in the dark to form a thin film. The cholesterol mixture was solubilized by adding 20 mM CD in MEM-HEPES buffer. The suspension was sonicated in a water bath (37° C.) for at 1 h, stirred at 37° C. for 3 h, filtered using a 0.45-µm syringe filter, and diluted with an equal volume of MEM-HEPES buffer containing 4 µg/mL Sandoz ACAT (acyl-CoA:cholesterol acyltransferase) inhibitor (Sigma). The final concentrations of BODIPY-cholesterol, unlabeled cholesterol, CD, and ACAT inhibitor in the labeling medium were 0.025 mM, 0.1 mM, 10 mM, and 2 mg/mL, respectively.

Preparation of efflux medium: Just before the initiation of the efflux assays, the human plasma frozen at −80° C. was thawed, and 80 µL of plasma was incubated with 20 µL of cyclic peptide stocks (peptide stocks were 1-3 mg/mL in 10% sucrose) or the vehicle (10% sucrose) at 37° C. for 30 min. The treated plasma samples (100 µL) were then incubated with 25% PEG 8000 solution in 200 mM glycine buffer, pH 8.5 (40 µL) to precipitate apoB-containing lipoproteins (Asztalos et al., J. Lipid Res. 46, 2246-2253, 2005). After a 15-min incubation, the precipitate was removed by high-speed centrifugation (13,000 rpm, 10 min, 4° C.), and the supernatant (60 µL) was immediately diluted with MEM-HEPES buffer (1.5 mL) to give ~2% whole plasma. This solution, containing the peptide remodeled-HDL lipoprotein fraction as cholesterol acceptors, was used as the efflux medium.

Cholesterol efflux from mouse macrophage cells: Mouse macrophage J774A.1 cells (TIB-67; American Type Culture Collection, Manassas, Va.) were seeded in 12-well culture plate at $3 \times 10^5$ cells/mL and cultured to 80-90% confluency in DMEM with 10% FBS at 5% $CO_2$. Cells were rinsed twice with MEM-HEPES, incubated for 1 h with 0.25 ml of labeling medium containing CD/BODIPY-cholesterol/unlabeled cholesterol and 2 µg/mL Sandoz ACAT inhibitor, followed by washing twice with MEM-HEPES. The cholesterol-laden cells were equilibrated for 18 h in DMEM containing 5% LPDS, 2 µm/mL Sandoz ACAT inhibitor, and 0.3 mM Cpt-cAMP. After equilibration, the cells were washed twice with MEM-HEPES and incubated with 0.25 mL of efflux media for 4 h. At the end of the incubation time, the efflux media was removed and centrifuged (1200 rpm, 10 min) to remove floating cells, and the fluorescence intensity of 100 µL cell-free media was recorded using a Tecan GENios plate reader (excitation 485 nm, emission 535 nm). The obtained signals were background subtracted using the signal from unlabeled cells. The cell monolayers were rinsed twice with ice-cold MEM-HEPES and solubilized with 0.25 mL 1% cholic acid by shaking on a plate shaker for at least 4 h at room temperature; then the fluorescence intensity of 100 µL cell lysate was recorded and background subtracted using the signal from unlabeled cell lysate. Fractional efflux of BODIPY-cholesterol was calculated based on the fluorescence intensity of the media divided by the total fluorescence values (medium+lysate). BODIPY-cholesterol efflux to the media containing vehicle (10% sucrose)-treated plasma was 29±0.7%, and was subtracted from cholesterol efflux values of all acceptors shown in FIG. 2. Measurements were made in quadruplicate.

Mouse Pharmacokinetics and In Vivo Plasma Remodeling

Pharmacokinetics: The TSRI Institutional Animal Care and Use Committee approved all experimental protocols involving live animals. Male mice (20 g) on a BALB/cByJ background were obtained from the Rodent Breeding Colony of the Department of Animal Resources at TSRI, and were maintained on a chow diet. The cyclic peptide c[wL-wReQeR], 1, was dissolved in PBS containing 1% sucrose, and sterile filtered through a 0.22-µm syringe filter before injection. Mice were fasted beginning 12 h before dosing, and continued the fast until after the 8-h time point blood draw was completed. Groups of three mice received a 16-mg/kg dose of the cyclic peptide via intraperitoneal injection (0.3 mL). Blood was drawn (30-60 µL) from the retro-orbital sinus into a heparinized capillary tube before dosing (0 min) and at different intervals from 30 min to 8 h after dosing. Plasma was isolated immediately from the whole blood by centrifugation at 5000 rpm for 10 min at 4° C. Immediately after the plasma was isolated, 20 µL, of plasma was acidified with 20 µL of 5% acetic acid to break peptide-protein interactions, and 40 µl of acetonitrile was then added. After vortexing for 30 s, the mixture was centrifuged at 13000 rpm for 10 min at 4° C. The resultant supernatant was analyzed by using LC-MS SIM as described below.

LC-MS SIM quantitation of peptide concentration: Cyclic peptide concentrations were quantified by using reverse-phase HPLC coupled with mass spectrometry. The electrospray ionization mass spectrometry measurements were carried out in the positive ionization mode using a single quadrupole mass spectrometer (Hewlett Packard HP 1100 MSD series). 10 or 20 μL of sample were injected through a C8 reverse-phase column (Zorbax 300-SB, 4.6 mm×150 mm, 5 μm) using a flow rate of 1.5 mL/min and binary gradients of solvent A (99% $H_2O$, 0.1% formic acid, 0.01% TFA) and solvent B (99% acetonitrile, 0.1% formic acid, 0.01% TFA). Mass detection was carried out in the selected ion monitoring (SIM) mode for the positive molecular ion, with the optimized fragmentor and capillary voltages of 180 V and 5 kV, respectively. The selected monitoring mass for cyclic peptide c[wLwReQeR] (SEQ ID NO:1), was 592.8 ($[M+2H]^{2+}$). For quantitative calibration, standard curves were established using mouse EDTA-anticoagulated plasma spiked with various concentrations of the peptide. The calibration curve was established by using linear fitting of the data, with correlation coefficient ≥0.98. The limit of detection was 1 μM.

In vivo plasma remodeling: Cyclic peptide c[wLwReQeR], 1, was dissolved in 10% sucrose, and sterile filtered through a 0.22-μm syringe filter before injection. Mice were fasted beginning 12 h before dosing, and continued the fast until after the 8-h time point blood draw was completed. Groups of three mice received a 20 mg/kg dose of the cyclic peptide via intraperitoneal injection (0.3 mL). Blood was drawn (30-60 μL) from the retro-orbital sinus into a heparinized capillary tube before dosing (0 min) and at different intervals from 30 min to 8 h after dosing. Plasma was isolated immediately from the whole blood by centrifugation at 5000 rpm for 10 min at 4° C., after which 10 μL of plasma were mixed with 90 μL of 50% sucrose, vortexed for 30 s, and stored at 4° C. until all time points had been collected (samples were stored from 0-8 h). Samples were then mixed with 20 μL of 6× native loading buffer (125 mM tris, pH 6.8, 0.02% bromophenol, 20% glycerol). 6 μL of these samples were loaded onto a 4-20% polyacrylamide gel. Gels were run at constant 80 V at 4° C. for 14 h using a Laemli buffer system (25 mM tris, 192 mM glycine, pH 8.3). Gels were then blotted onto nitrocellulose membranes (0.45 μm, Bio-Rad) at constant 30 V at 4° C. for 2 h using the Laemli buffer (no methanol). The membrane was blocked with 5% non-fat dry milk (NFDM) in TBST (20 mM tris, 150 mM NaCl, pH 7.6, 0.1% Tween-20) for 1 h at 23° C., and then washed once for 10 min with TBST. The membrane was next incubated with 1% NFDM in TBST containing a 1:5,000 dilution of rabbit anti-mouse apoA-I antibody (Meridian Life Science) as primary antibody for 1 h at 23° C. The membrane was extensively washed with TBST (at least 6×10 min), and incubated with 1% NFDM containing a ~1:50,000 dilution of HRP-conjugated anti-rabbit IgG (Thermo) as secondary antibody for 1 h at 23° C. The membrane was extensively washed with TBST (at least 6×10 min), and once with TBS. The membrane was incubated with ECL reagent (Thermo SuperSignal West Pico) for 5 min, and then imaged using photographic film (Kodak BioMax Light).

In vivo efficacy study: LDL receptor-null ($LDLr^{-/-}$) mice on a C57BL/6J background were initially purchased from Jackson Laboratories (Bar Harbor, Me.) and were bred in house. The mice were weaned at 4 weeks of age and were fed ad libitum a standard chow diet (Harlan Teklad 7019) until they were 10-weeks old, when they were switched to a high-fat Western diet (WD) containing 15.8% (wt/wt) fat, 1.25% (wt/wt) cholesterol, and no cholate (Harlan Teklad 94059). At the time that the WD was started, the test cyclic peptide was added to the drinking water at a high dose of 180 μM (200 μg/mL) or a low dose of 18 μM (20 μg/mL) and the mice (female, n=8 per dosing group) were continued on WD for 10 weeks. The lyophilized peptide was easily dissolved in PBS (pH 7.4) containing 1% sucrose, resulting in a clear solution. The drinking water solution was replaced with fresh solution every day. A control group of eight mice (female, n=8) were fed WD with vehicle (PBS with 1% sucrose) drinking water. The mice consumed approximately 2.5 mL of water per day per mouse, and there was no significant difference in water or food consumption between groups. The feeding and treatment schedule for the in vivo efficacy study is shown in FIG. 6.

Effect of cyclic peptides on plasma total cholesterol: The mice were bled after two weeks of treatment and at the time of harvest (10 weeks). The blood (200 μL) was collected after an overnight fast (14-16 h) by retro-orbital puncture into a heparinized capillary tube at two weeks, or by cardiac puncture into EDTA anti-coagulant coated tubes at the time of harvest (10 weeks). Plasma was separated from whole blood immediately by centrifugation of the blood samples at 5000 rpm for 10 min at 4° C., and was then stored at −80° C. Plasma total cholesterol (TC) was measured using an enzymatic colorimetric method kit (Amplex® red cholesterol assay kit, No. A12216, Life Technologies) according to the manufacturer's instructions.

Effect of cyclic peptides on plasma lipoprotein and lipoprotein cholesterol profiles: Pooled plasma (240 μL total, 30 μL from each, n=8 mice per group) from the two-week blood draw was used for fast protein liquid chromatography (FPLC) analysis. Lipoproteins were separated by using 3 Superdex 200 10/30 columns connected in series (GE Healthcare). The plasma was centrifuged at 11,000 rpm for 10 min at room temperature to remove particulates (floating material was gently mixed into liquid before removing the supernatant for FPLC injection). 200 μL of the pooled plasma was injected on the system eluted with 10 mM tris-HCl buffer, pH 7.4, containing 1 mM EDTA and 150 mM NaCl; a flow rate of 0.5 ml/min and fraction size of 0.5 mL were used. Total cholesterol in the FPLC fractions was measured using the Amplex® red cholesterol assay kit (No. A12216, Life Technologies) according to the manufacturer's instructions. 20 μL of selected HDL fractions (as indicated in FIG. 6) were mixed with 4 μL of 6× native loading buffer (375 mM tris, pH 6.8, 0.06% bromophenol, 60% glycerol), out of which 20 μL was applied to non-denaturing gel electrophoresis and then immunoblotted for mouse apoA-I as described above.

Evaluation of atherosclerosis: Atherosclerotic lesion severity was assessed in the aortae as previously described in Mullick et al., J. Clin. Invest. 115, 3149-3156, 2005. Briefly, at euthanasia, animals were perfused with PBS, followed by 4% formaldehyde (10% UltraPure EM Grade from Polysciences diluted in PBS, pH 7.2). For en face analysis, the entire mouse aorta was dissected from the proximal ascending aorta to the bifurcation of the iliac artery by using a dissecting microscope. Adventitial fat was removed, and the aorta was opened longitudinally, pinned flat onto black dissecting wax, stained with Sudan IV, and photographed at a fixed magnification. The photographs were digitized, and total aortic areas and lesion areas were calculated by using Adobe Photoshop version CS4, Chromatica V, and NIH Scion Image software (http://rsb.info-.nih.gov/nih-image/Default.html). The results were reported as a percentage of the total aortic area that contained lesions.

As a second assessment of atherosclerosis, lesions of the aortic root (heart sinus) were analyzed. Utilizing stereological principles, lesion volume was estimated across a fixed distance of the aortic sinus. After 10 min fixation in 4% paraformaldehyde, hearts were cut at an angle perpendicular to the atria of the heart and embedded in OCT (Tissue-Tek). Frozen hearts were sectioned on a Leica cryostat, with 10-μm sections collected from the beginning of the aortic sinus (defined as when a valve leaflet became visible) to 500 μm below the beginning of the sinus. For hearts cut at an angle that resulted in valve leaflets not appearing in the same section (due to poor section angle), the lagging leaflet was used to determine the 500-μm distance. Sections were collected in duplicate at 50-μm intervals. Sections were stained with oil red O, counterstained with Gill hematoxylin 1 (Fischer Scientific International), photographed, and digitized for lesion analysis. Scoring of valve lesion areas was done for each of the 3 valve cusps individually. Lesion areas found only within the valve cusp were measured. Lesion volume estimation was determined from a 1-in-10 sampling rate; hence, valve cusps spaced at 140 μm were used to determine the lesion volume for a total of four sections analyzed per valve cusp. Lesion volume was calculated from an integration of the measured cross-sectional areas. Prediction of the coefficient of error (CE) in approximating lesion volume was computed using the Cavalieri estimator derived from a covariogram analysis of an ordered set of estimates of cross-sectional areas. This yielded CE values of less than 10% that were acceptable for a stereological computation of lesion volume.

Body, liver, and spleen weights: Food and water intake in the control and treated groups were comparable. Body weight was measured weekly. Mice were weighed prior to fasting. Liver and spleen weights were determined at the end of treatment.

Plasma liver enzyme activities: At the time of harvest (10 week), blood (~0.5 mL) was collected after an overnight fast (14-16 h) by cardiac puncture into EDTA anti-coagulant coated tubes, and centrifuged at 4° C. for 10 min×5000 rpm. Plasma samples were stored at −80° C. until analysis. Plasma alanine aminotransferase (ALT) and aspartate aminotransferase (AST) concentrations were measured using Infinity ALT (GPT) and AST (GOT) liquid stable reagents, respectively, which is a colorimetric kinetic assay (Thermo Scientific). Assays were performed in accordance to the manufacturer's recommendations, adjusting the reagent volumes (20 μL plasma+200 μL reagent, 0.69-cm light pathlength of the solution in the well) for analysis of samples in 96-well flat bottom microplate format.

Example 6 Further Studies of Anti-Atherosclerotic Activities

This Example describes some additional in vivo studies on the cholesterol reducing and atherosclerosis inhibiting activities of the cyclic peptides of the invention.

First, various cyclic peptides, including the majority of compounds shown in FIG. 2, were assessed for activities for remodeling HDL in human plasma in vitro. Unlike western blot which was used to generate data shown in FIG. 2, here a pre-beta HDL ELISA assay was used to measure pre-beta HDL levels. Results from the assay are shown in Table 1, which lists the peptides in the order of their activities in remodeling HDL.

Figure 7:
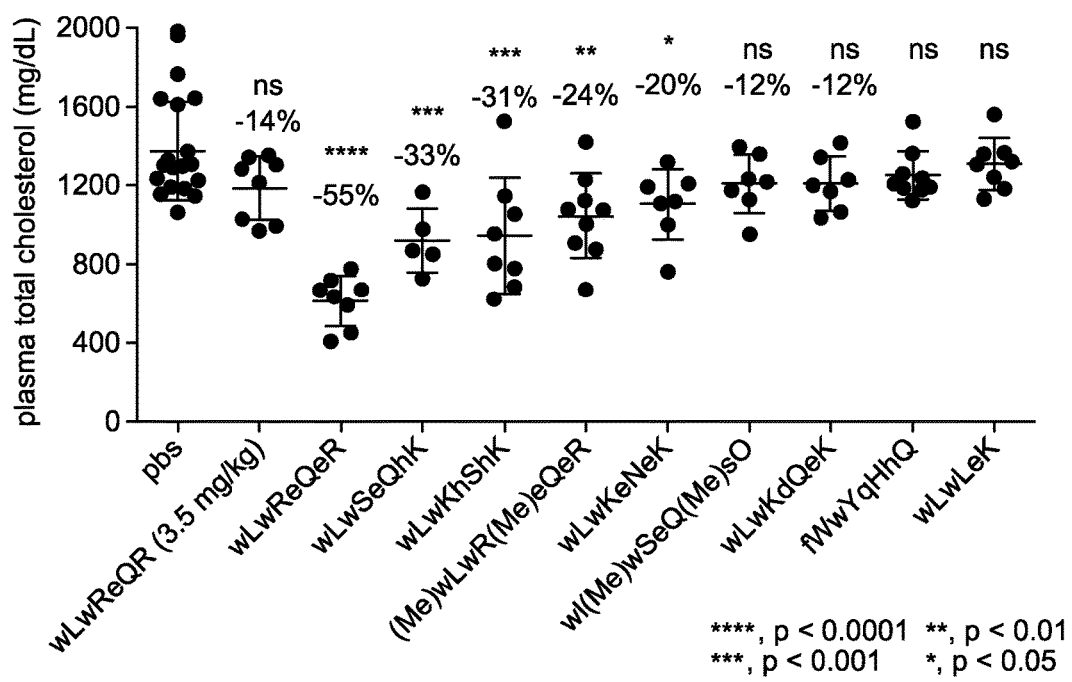
FIG. 7 shows that oral administration of several peptides can significantly reduce plasma cholesterol levels in mice. Cyclic peptides used in the study are wLwReQeR (SEQ ID NO:1), wLwSeQhK (SEQ ID NO:40), wLwKhShK (SEQ ID NO:53), (Me)wLwR(Me)eQeR (SEQ ID NO:46), wLwKeNeK (SEQ ID NO:11), wL(Me)wSeQ(Me)sO (SQE ID NO:14), wLwKdQeK (SEQ ID NO:2), fWwYqHhQ (SEQ ID NO:5), and wLwLeK (SEQ ID NO:81).

In addition, several peptides were administered orally to mice at a 35 mg/kg dose (unless otherwise noted) in the drinking water for two weeks. The female LDLr-null mice maintained on a high-fat diet were provided with peptide-treated 1% sucrose/PBS or 1% sucrose/PBS alone as the drinking water ad libitum. Cholesterol levels were then determined. The data are shown in FIG. 7 as a scatter plot along with mean±SD. p values were determined by the one-way ANOVA test with a post hoc Tukey-Kramer test. As shown in the figure, the results indicate that the peptides significantly reduced plasma cholesterol levels in vivo.

Other than their in vivo cholesterol reducing activities, several peptides were also examined for ability to inhibit development of atherosclerotic legions in vivo. Female high-fat-fed LDLr-null mice were orally administered with the peptides in drinking water ad libitum for 10 weeks. As shown in FIG. 8, several peptides at a 35-mg/kg dose were able to reduce the development of whole aorta lesion areas and aortic sinus lesion volumes. At a 10-fold lower dose, peptide wLwReQeR (SEQ ID NO:1) had no significant effect on lesions. The results are shown in FIG. 8. All charts in the figure are shown as a scatter plot along with mean±SD. p values were determined by the one-way ANOVA test with a post hoc Tukey-Kramer test.

Figure 9:
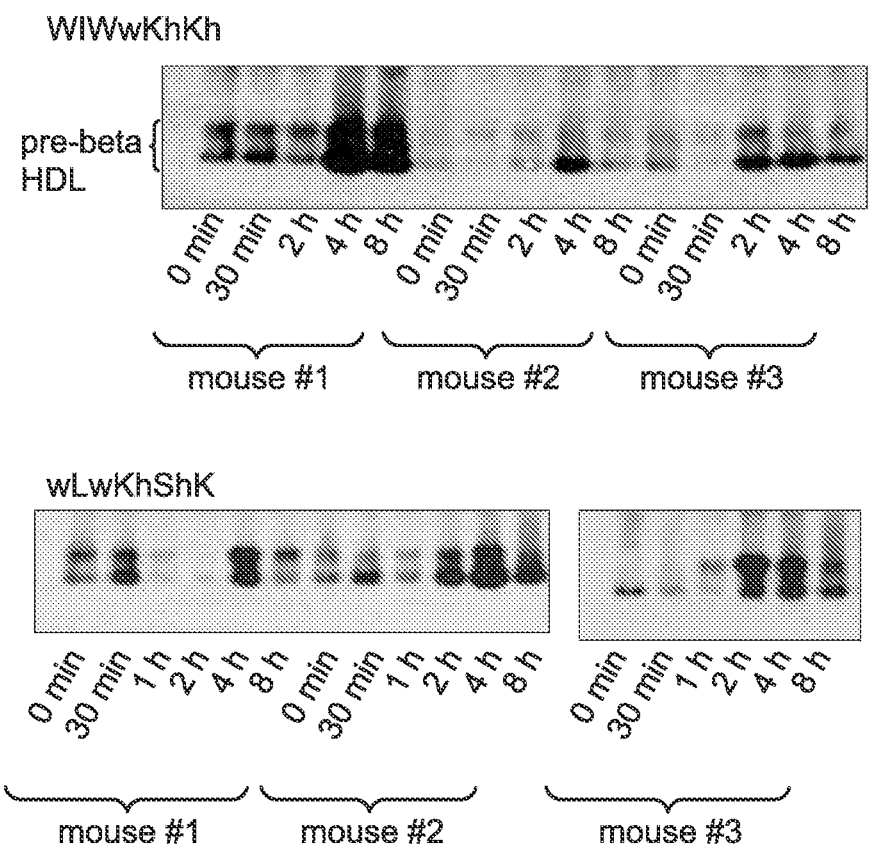
FIG. 9 shows in vivo HDL remodeling activities of selected cyclic peptides. The cyclic used in the study are WIWwKhKh (SEQ ID NO:82) and wLwKhShK (SEQ ID NO:53).

In vivo plasma HDL remodeling activities of some of the peptides were also analyzed. The peptides were administered to male mice (n=3) via intraperitoneal injection (18-24 mg/kg). As shown in FIG. 9, several peptides (e.g., peptides with sequences shown in SEQ ID NOs:53 and 82) were able to remodel plasma HDL to increase the level of lipid-poor pre-beta particles. Results shown in the figure were determined by Western blotting for mouse apoA-I.

Backbone alkylation in cyclic D,L-alpha peptides is known to prevent the formation of nanotubes. Backbone alkylation can also improve oral bioavailability of peptides. It was found that backbone alkylation may negatively affect the peptide's activity in reducing plasma cholesterol levels in vivo and promoting the formation of pre-beta HDL levels in vitro. This is evidenced by the activities of peptide (Me) wLwR(Me)eQeR (SEQ ID NO:46), which is a methylation derivative of c[wLwReQeR] (SEQ ID NO:1), as shown in FIG. 7 and Table 1. Surprisingly, the methylated derivative peptide nonetheless remains very effective as the parent compound in preventing the development of atherosclerotic lesions, as shown in FIG. 8.

TABLE 1

Rank order of peptides in generating pre-beta HDL in human plasma in vitro

| Peptide Sequence | SEQ ID NO: | Pre-beta HDL generated (normalized level) | Peptide rank |
| --- | --- | --- | --- |
| fWwYtRhS | 51 | 1.44 | 1 |
| fWwYqHhQ | 5 | 1.29 | 2 |
| wLwReQeR | 1 | 0.88 | 3 |
| WlWwKhKh | 47 | 0.79 | 4 |
| wLwKhShK | 53 | 0.79 | 5 |
| wFyYhOrS | 48 | 0.70 | 6 |
| (PA)wLlHsKk | 49 | 0.67 | 7 |
| wLwSeQsO | 4 | 0.59 | 8 |
| WlWrEqEr | 50 | 0.54 | 9 |
| wFfYrHhS | 52 | 0.52 | 10 |
| YlWyKhAe | 15 | 0.51 | 11 |
| wLwRdNdK | 9 | 0.47 | 12 |
| wLwReQeR | 54 | 0.46 | 13 |
| wLwOeQeO | 13 | 0.46 | 14 |
| wLwSeQhK | 40 | 0.40 | 15 |
| wLlwKdDk | 26 | 0.36 | 16 |

TABLE 1-continued

Rank order of peptides in generating pre-beta HDL in human plasma in vitro

| Peptide Sequence | SEQ ID NO: | Pre-beta HDL generated (normalized level) | Peptide rank |
|---|---|---|---|
| wLwOeNeO | 19 | 0.36 | 17 |
| LwLwLrKe | 6 | 0.36 | 18 |
| w(Nal)wReQeR | 28 | 0.35 | 19 |
| LwLwLsEk | 55 | 0.35 | 20 |
| fFyYsRkO | 56 | 0.31 | 21 |
| wLwKsK | 57 | 0.30 | 22 |
| (py)LwKsKsK | 58 | 0.27 | 23 |
| wLwKdNdK | 8 | 0.26 | 24 |
| wLwKeNeK | 11 | 0.24 | 25 |
| wYwYsRss | 59 | 0.24 | 26 |
| w(NB)kSkSkS | 60 | 0.20 | 27 |
| yAyLkHkK | 61 | 0.19 | 28 |
| yWyKsHaE | 25 | 0.19 | 29 |
| yYvYhH | 62 | 0.17 | 30 |
| wLwReNeO | 23 | 0.16 | 31 |
| wFwYrSsH | 64 | 0.16 | 32 |
| w(Aoc)wSeQsO | 22 | 0.13 | 33 |
| wLwKdQdK | 10 | 0.12 | 34 |
| yGwWnNkN | 65 | 0.11 | 35 |
| w(BY)kNnKkK | 66 | 0.10 | 36 |
| wLwKdQeK | 2 | 0.10 | 37 |
| wLwHeQeH | 24 | 0.09 | 38 |
| YwElYsKq | 16 | 0.09 | 39 |
| w(hLu)wReQeR | 67 | 0.08 | 40 |
| YwDsKh | 17 | 0.08 | 41 |
| yDyWyHaK | 34 | 0.08 | 42 |
| wLwHeNeK | 12 | 0.07 | 43 |
| wWfYkHsS | 68 | 0.07 | 44 |
| lWlHeKkH | 69 | 0.07 | 45 |
| wLlEeKkN | 20 | 0.07 | 46 |
| LlWlKkKk | 70 | 0.06 | 47 |
| WgWgWkSo | 71 | 0.06 | 48 |
| wLwSeQsK | 30 | 0.06 | 49 |
| lWkHsHkK | 72 | 0.04 | 50 |
| w(Aoc)wReQeR | 31 | 0.04 | 51 |
| LwLhKkEh | 73 | 0.04 | 52 |
| fFyFkK | 74 | 0.04 | 53 |
| wLw(Dap)eQeK | 75 | 0.03 | 54 |
| lWlKkKhR | 76 | 0.03 | 55 |
| WfElYsHo | 77 | 0.02 | 56 |
| wLwReQeO | 35 | 0.02 | 57 |
| yLwKkK | 78 | 0.01 | 58 |
| wLkSkSkS | 79 | 0.01 | 59 |
| wLwRdQeK | 80 | 0.01 | 60 |

$^a$ Upper case letters represent L amino acids, lower case letters represent D amino acids. Abbreviations of unusual amino acids: PA, 4-pyridylalanine; Me, methylated backbone amide; O, ornithine; Nal, 1-naphthylalanine; PY, 3-pyridylalanine; NB, 2-naphthylalanine; Aoc, 2-aminooctanoic acid; BY, benzyltyrosine; hLu, homoleucine; Dap, 2,3-diaminopropionic acid; CPn, Cys alkylated with pentyl chain; KB, benzyllysine; Dab, 2,4-diaminobutyric acid.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

SEQUENCE LISTING

<160> NUMBER OF SEQ ID NOS: 82

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues. 1st residue (w) is D-Trp, 2nd
      residue is an L-Leu, and etc. In the specification, lowercase
      letters= D residues, uppercase letters= L residues for all
      sequences herein.

<400> SEQUENCE: 1

Trp Leu Trp Arg Glu Gln Glu Arg
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues. 1st residue (w) is D-Trp, 2nd
      residue is an L-Leu, and so on.

```
<400> SEQUENCE: 2

Trp Leu Trp Lys Asp Gln Glu Lys
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue (w) is D-Trp, 2nd
      residue is an L-Leu, and so on.

<400> SEQUENCE: 3

Trp Leu Trp Arg Asp Gln Glu Lys
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue (w) is D-Trp, 2nd
      residue is an L-Leu, and so on.
<220> FEATURE:
<221> NAME/KEY: MISC_FEATURE
<222> LOCATION: (8)..(8)
<223> OTHER INFORMATION: Xaa is ornithine

<400> SEQUENCE: 4

Trp Leu Trp Ser Glu Gln Ser Xaa
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 5

Phe Trp Trp Tyr Gln His His Gln
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.
```

<400> SEQUENCE: 6

Leu Trp Leu Trp Leu Arg Lys Glu
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 7

Trp Leu Trp Glx Glu Gln Glu Lys
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 8

Trp Leu Trp Lys Asp Asn Asp Lys
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 9

Trp Leu Trp Arg Asp Asn Asp Lys
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: METAL
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 10

Trp Leu Trp Lys Asp Gln Asp Lys
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 11

Trp Leu Trp Lys Glu Asn Glu Lys
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 12

Trp Leu Trp His Glu Asn Glu Lys
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (4)..(8)
<223> OTHER INFORMATION: Xaa is ornithine.

<400> SEQUENCE: 13

Trp Leu Trp Xaa Glu Gln Glu Xaa
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE

```
<222> LOCATION: (3)..(3)
<223> OTHER INFORMATION: Xaa is N-methylated Trp.
<220> FEATURE:
<221> NAME/KEY: MISC_FEATURE
<222> LOCATION: (7)..(7)
<223> OTHER INFORMATION: Xaa is N-methylated Ser.
<220> FEATURE:
<221> NAME/KEY: MISC_FEATURE
<222> LOCATION: (8)..(8)
<223> OTHER INFORMATION: Xaa is ornithine.

<400> SEQUENCE: 14

Trp Leu Xaa Ser Glu Gln Xaa Xaa
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.

<400> SEQUENCE: 15

Tyr Leu Trp Tyr Lys His Ala Glu
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a DL-residue, and so on.

<400> SEQUENCE: 16

Tyr Trp Glu Leu Tyr Ser Lys Gln
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating L- and D-residues.  1st residue is an L-residue, 2nd
      residue is a D-residue, and so on.

<400> SEQUENCE: 17

Tyr Trp Asp Ser Lys His
1               5

<210> SEQ ID NO 18

<400> SEQUENCE: 18

000
```

```
<210> SEQ ID NO 19
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (4)..(8)
<223> OTHER INFORMATION: Xaa is ornithine.

<400> SEQUENCE: 19

Trp Leu Trp Xaa Glu Asn Glu Xaa
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 20

Trp Leu Leu Glu Glu Lys Lys Asn
1               5

<210> SEQ ID NO 21

<400> SEQUENCE: 21

000

<210> SEQ ID NO 22
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is 2-amino-octanoic acid.
<220> FEATURE:
<221> NAME/KEY: MISC_FEATURE
<222> LOCATION: (8)..(8)
<223> OTHER INFORMATION: Xaa is ornithine.

<400> SEQUENCE: 22

Trp Xaa Trp Ser Glu Gln Ser Xaa
1               5

<210> SEQ ID NO 23
```

```
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 23

Trp Leu Trp Arg Glu Asn Glu Xaa
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 24

Trp Leu Trp His Glu Gln Glu His
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 25

Tyr Trp Tyr Lys Ser His Ala Glu
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 26

Trp Leu Leu Trp Lys Asp Asp Lys
1               5
```

<210> SEQ ID NO 27

<400> SEQUENCE: 27

000

<210> SEQ ID NO 28
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequenc is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is naphthylalanine.

<400> SEQUENCE: 28

Trp Xaa Trp Arg Glu Gln Glu Arg
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is homoleucine.

<400> SEQUENCE: 29

Trp Xaa Trp Arg Glu Gln Glu Arg
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 30

Trp Leu Trp Ser Glu Gln Ser Lys
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic sequence
<220> FEATURE:

```
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is 2-aminooctanoic acid.

<400> SEQUENCE: 31

Trp Xaa Trp Arg Glu Gln Glu Arg
1               5

<210> SEQ ID NO 32

<400> SEQUENCE: 32

000

<210> SEQ ID NO 33

<400> SEQUENCE: 33

000

<210> SEQ ID NO 34
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.

<400> SEQUENCE: 34

Tyr Asp Tyr Trp Tyr His Ala Lys
1               5

<210> SEQ ID NO 35
<211> LENGTH: 8
<212> TYPE: PRT
<213> ORGANISM: ARTIFICIAL SEQUENCE
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 35

Trp Leu Trp Arg Glu Gln Glu Xaa
1               5

<210> SEQ ID NO 36

<400> SEQUENCE: 36

000
```

```
<210> SEQ ID NO 37
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 37

Trp Leu Trp Glu Arg Gln Arg Glu
1               5

<210> SEQ ID NO 38

<400> SEQUENCE: 38

000

<210> SEQ ID NO 39

<400> SEQUENCE: 39

000

<210> SEQ ID NO 40
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 40

Trp Leu Trp Ser Glu Gln His Lys
1               5

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44
<211> LENGTH: 8
<212> TYPE: PRT
<213> ORGANISM: Artificial sequence
<220> FEATURE:
<223> OTHER INFORMATION: Synthetic sequence
```

```
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 44

Trp Leu Trp His Glu Gln Glu Lys
1               5

<210> SEQ ID NO 45
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 45

Trp Leu Trp Ser Glu Gln Ser Xaa
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (1)..(1)
<223> OTHER INFORMATION: Xaa is N-methylated tryptophan.
<220> FEATURE:
<221> NAME/KEY: MISC_FEATURE
<222> LOCATION: (5)..(5)
<223> OTHER INFORMATION: Xaa is N-methylated glutamic acid.

<400> SEQUENCE: 46

Xaa Leu Trp Arg Xaa Gln Glu Arg
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising both D-
      and L-residues. The first 3 residues are L-residues, and the last
      5 residues are D-residues.

<400> SEQUENCE: 47

Trp Ile Trp Trp Lys His Lys His
```

<210> SEQ ID NO 48
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (6)..(6)
<223> OTHER INFORMATION: Xaa is ornithine.

<400> SEQUENCE: 48

Trp Phe Tyr Tyr His Xaa Arg Ser
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (1)..(1)
<223> OTHER INFORMATION: Xaa is 4-pyridylalanine.

<400> SEQUENCE: 49

Xaa Trp Leu Leu His Ser Lys Lys
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising both L-
      and D-residues. The 4th, 6th and 8th residues are D-residues, and
      the others L-residues.

<400> SEQUENCE: 50

Trp Ile Trp Arg Glu Gln Glu Arg
1               5

<210> SEQ ID NO 51
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd residue is an L-residue, and so on.

<400> SEQUENCE: 51

Phe Trp Trp Tyr Thr Arg His Ser
1               5

<210> SEQ ID NO 52
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 52

Trp Phe Phe Tyr Arg His His Ser
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 53

Trp Leu Trp Lys His Ser His Lys
1               5

<210> SEQ ID NO 54
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 54

Trp Leu Trp Arg Glu Gln Glu Arg
1               5

<210> SEQ ID NO 55
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.

<400> SEQUENCE: 55

```
Leu Trp Leu Trp Leu Ser Glu Lys
1               5

<210> SEQ ID NO 56
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 56

Phe Phe Tyr Tyr Ser Arg Lys Xaa
1               5

<210> SEQ ID NO 57
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating D- and L-residues.  1st residue is a D-residue, 2nd
      residue is an L-residue, and so on.

<400> SEQUENCE: 57

Trp Leu Trp Lys Ser Lys
1               5

<210> SEQ ID NO 58
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (1)..(1)
<223> OTHER INFORMATION: Xaa is 3-pyridylalanine.

<400> SEQUENCE: 58

Xaa Leu Trp Lys Ser Lys Ser Lys
1               5

<210> SEQ ID NO 59
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
```

```
<223> OTHER INFORMATION: Sequence is a cyclic peptide comprising both D-
      and L-residues. The 2nd, 4th and 6th residues are L-residues, and
      the others being D-residues.

<400> SEQUENCE: 59

Trp Tyr Trp Tyr Ser Arg Ser Ser
1               5

<210> SEQ ID NO 60
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is 2-naphthylalanine.

<400> SEQUENCE: 60

Trp Xaa Lys Ser Lys Ser Lys Ser
1               5

<210> SEQ ID NO 61
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 61

Tyr Ala Tyr Leu Lys His Lys Lys
1               5

<210> SEQ ID NO 62
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating D- and L-residues.  1st residue is a D-residue, 2nd
      residue is an L-residue, and so on.

<400> SEQUENCE: 62

Tyr Tyr Val Tyr His His
1               5

<210> SEQ ID NO 63

<400> SEQUENCE: 63

000

<210> SEQ ID NO 64
```

```
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 64

Trp Phe Trp Tyr Arg Ser Ser His
1               5

<210> SEQ ID NO 65
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 65

Tyr Gly Trp Trp Asn Asn Lys Asn
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is benzyltyrosine.

<400> SEQUENCE: 66

Trp Xaa Lys Asn Asn Lys Lys Lys
1               5

<210> SEQ ID NO 67
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (2)..(2)
<223> OTHER INFORMATION: Xaa is homoleucine.

<400> SEQUENCE: 67
```

```
Trp Xaa Trp Arg Glu Gln Glu Arg
1               5
```

<210> SEQ ID NO 68
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 68

```
Trp Trp Phe Tyr Lys His Ser Ser
1               5
```

<210> SEQ ID NO 69
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 69

```
Leu Trp Leu His Glu Lys Lys His
1               5
```

<210> SEQ ID NO 70
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.

<400> SEQUENCE: 70

```
Leu Leu Trp Leu Lys Lys Lys Lys
1               5
```

<210> SEQ ID NO 71
<211> LENGTH: 8
<212> TYPE: PRT
<213> ORGANISM: ARTIFICIAL SEQUENCE
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 71

```
Trp Gly Trp Gly Trp Lys Ser Xaa
1               5

<210> SEQ ID NO 72
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 72

Leu Trp Lys His Ser His Lys Lys
1               5

<210> SEQ ID NO 73
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.

<400> SEQUENCE: 73

Leu Trp Leu His Lys Lys Glu His
1               5

<210> SEQ ID NO 74
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating D- and L-residues.  1st residue is a D-residue, 2nd
      residue is an L-residue, and so on.

<400> SEQUENCE: 74

Phe Phe Tyr Phe Lys Lys
1               5

<210> SEQ ID NO 75
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.
<220> FEATURE:
<221> NAME/KEY: MISC_FEATURE
<222> LOCATION: (4)..(4)
<223> OTHER INFORMATION: X is 2,3-diaminopropionic acid.
```

```
<400> SEQUENCE: 75

Trp Leu Trp Xaa Glu Gln Glu Lys
1               5

<210> SEQ ID NO 76
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 76

Leu Trp Leu Lys Lys Lys His Arg
1               5

<210> SEQ ID NO 77
<211> LENGTH: 8
<212> TYPE: PRT
<213> ORGANISM: ARTIFICIAL SEQUENCE
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating L- and D-residues.  1st residue is an L-residue, 2nd
      residue is a D-residue, and so on.
<220> FEATURE:
<221> NAME/KEY: MISC_FEATURE
<222> LOCATION: (8)..(8)
<223> OTHER INFORMATION: Xaa is ornithine.

<400> SEQUENCE: 77

Trp Phe Glu Leu Tyr Ser His Xaa
1               5

<210> SEQ ID NO 78
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating D- and L-residues.  1st residue is a D-residue, 2nd
      residue is an L-residue, and so on.

<400> SEQUENCE: 78

Tyr Leu Trp Lys Lys Lys
1               5

<210> SEQ ID NO 79
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
```

```
<400> SEQUENCE: 79

Trp Leu Lys Ser Lys Ser Lys Ser
1               5

<210> SEQ ID NO 80
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising
      alternating D- and L-residues.  1st residue is a D-residue, 2nd
      residue is an L-residue, and so on.

<400> SEQUENCE: 80

Trp Leu Trp Arg Asp Gln Glu Lys
1               5

<210> SEQ ID NO 81
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: Sequence is a cyclic peptide comprising
      alternating D- and L-residues.  1st residue is a D-residue, 2nd
      residue is an L-residue, and so on.

<400> SEQUENCE: 81

Trp Leu Trp Leu Glu Lys
1               5

<210> SEQ ID NO 82
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: Sequence is a cyclic peptide comprising both D-
      and L-residues. The 4th, 6th and 8th residues are D-residues, and
      the others being L-residues.

<400> SEQUENCE: 82

Trp Ile Trp Trp Lys His Lys His
1               5
```

What is claimed is:

1. A method for treating or preventing atherosclerosis or a disorder associated with or mediated by atherosclerosis, comprising administering to a subject afflicted with or at risk of developing atherosclerosis, or a disorder associated with or mediated by atherosclerosis, a therapeutically effective amount of a pharmaceutical composition comprising a cyclic peptide consisting of about eight alternating D- and L-amino acid residues or analogs along its entire sequence, wherein the cyclic peptide compound has a sequence formula of c[B-J-U1-X-U2-Z], wherein B consists of $^D$Trp-Leu-$^D$Trp or $^D$Tyr-Leu-$^D$Tyr; J is Lys, Arg, or Ser; U1 and U2 are each independently a $^D$Asp, $^D$Glu or $^D$Ser residue; X is Asn or Gln; and Z is Lys, Arg, Orn (ornithine) or diaminobutyric acid.

2. A method for treating or preventing atherosclerosis or a disorder associated with or mediated by atherosclerosis, comprising administering to a subject afflicted with or at risk of developing atherosclerosis, or a disorder associated with or mediated by atherosclerosis, a therapeutically effective amount of a pharmaceutical composition comprising a cyclic peptide having alternating D- and L-residues along its partial or entire sequence, wherein the cyclic peptide is selected from the group consisting of c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[fWwY-qHhQ] (SEQ ID NO:5), c[LwLwLrKe] (SEQ ID NO:6), c[wLwZeQeK] (SEQ ID NO:7), c[wLwKdNdK] (SEQ ID NO:8), c[wLwRdNdK] (SEQ ID NO:9), c[wLwKdQdK]

(SEQ ID NO:10), c[wLwKeNeK] (SEQ ID NO:11), c[wLwHeNeK] (SEQ ID NO:12), c[wLwOeQeO] (SEQ ID NO:13), c[wLMewSeQMesO] (SEQ ID NO:14), and c[wLwOeNeO] (SEQ ID NO:19), c[w(Aoc)wSeQsO] (SEQ ID NO:22), c[wLwReNeO] (SEQ ID NO:23), c[wLwHeQeH] (SEQ ID NO:24), c[yWyKsHaE] (SEQ ID NO:25), c[wL1wKdDk] (SEQ ID NO:26), c[w(Nal)wReQeR] (SEQ ID NO:28), c[w(Hml)wReQeR] (SEQ ID NO:29), c[wLwSeQhK] (SEQ ID NO:40), c[(Me)wLwR(Me)eQeR] (SEQ ID NO:46), c[WIWwkhkh] (SEQ ID NO:47), c[wFyYhOrS] (SEQ ID NO:48), c[(PA)wL1HsKk] (SEQ ID NO:49), c[WIWrEqEr] (SEQ ID NO:50), c[fWwYtRhS (SEQ ID NO:51)], c[wFfYrHhS] (SEQ ID NO:52), and c[wLwKhShK] (SEQ ID NO:53), and conservatively substituted sequences thereof.

3. The method of claim 2, wherein the cyclic peptide comprises a sequence of c[wLwReQeR] (SEQ ID NO:1), c[wLwSeQsO] (SEQ ID NO:4), or c[wLwSeQhK] (SEQ ID NO:40).

4. A method for treating or preventing atherosclerosis or a disorder associated with or mediated by atherosclerosis, comprising administering to a subject afflicted with or at risk of developing atherosclerosis, or a disorder associated with or mediated by atherosclerosis, a therapeutically effective amount of a pharmaceutical composition comprising a cyclic peptide, wherein the cyclic peptide compound has a sequence formula of c[wLw-J-u1-X-u2-Z] and comprises about 8 alternating D- and L-form of amino acid residues or amino acid analogs, wherein "wLw" denotes a tripeptide segment consisting of $^D$Trp-Leu-$^D$Trp; J is serine or a positively charged amino acid residue or analog; u1 and u2 are each independently a $^D$Asp, $^D$Glu or $^D$Ser residue; X is Asn residue or Gln residue; and Z is a positively charged amino acid residue or analog.

5. The method of claim 4, wherein J is Lys, Arg, His, Ser, Orn (ornithine), diaminobutyric acid or diaminopropionic acid.

6. The method of claim 4, wherein Z is Lys, Arg, or Orn (ornithine).

7. The method of claim 4, wherein the cyclic peptide is selected from the group consisting of c[wLwReQeR] (SEQ ID NO:1), c[wLwKdQeK] (SEQ ID NO:2), c[wLwRdQeK] (SEQ ID NO:3), c[wLwSeQsO] (SEQ ID NO:4), c[wLwZeQeK] (SEQ ID NO:7), c[wLwKdNdK] (SEQ ID NO:8), c[wLwRdNdK] (SEQ ID NO:9), c[wLwKdQdK] (SEQ ID NO:10), c[wLwKeNeK] (SEQ ID NO:11), c[wLwHeNeK] (SEQ ID NO:12), c[wLwOeQeO] (SEQ ID NO:13), and c[wLwOeNeO] (SEQ ID NO:19).

* * * * *

UNITED STATES PATENT AND TRADEMARK OFFICE
CERTIFICATE OF CORRECTION

PATENT NO. : 10,092,620 B2
APPLICATION NO. : 14/781859
DATED : October 9, 2018
INVENTOR(S) : Ghadiri et al.

Page 1 of 1

It is certified that error appears in the above-identified patent and that said Letters Patent is hereby corrected as shown below:

In the Specification

Column 1, Line 14, the paragraph STATEMENT OF GOVERNMENT SUPPORT should be changed to:
-- STATEMENT OF GOVERNMENT LICENSE RIGHTS
This invention was made with government support under grant numbers HL104462 and HL118114 awarded by the National Institutes of Health. The government has certain rights in the invention. --

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*